United States Patent
Kanayama et al.

(10) Patent No.: US 8,480,584 B2
(45) Date of Patent: *Jul. 9, 2013

(54) NON-INVASIVE SUBJECT-INFORMATION IMAGING METHOD AND APPARATUS

(75) Inventors: Shoichi Kanayama, Koshigaya (JP); Kazuhiro Itsumi, Kawasaki (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 0 days.
This patent is subject to a terminal disclaimer.

(21) Appl. No.: 12/950,689

(22) Filed: Nov. 19, 2010

(65) Prior Publication Data
US 2011/0066023 A1    Mar. 17, 2011

Related U.S. Application Data

(63) Continuation of application No. 10/812,884, filed on Mar. 31, 2004, now Pat. No. 8,353,830.

(30) Foreign Application Priority Data

Feb. 6, 2004    (JP) .................................. 2004-030578

(51) Int. Cl.
*A61B 8/00*    (2006.01)
(52) U.S. Cl.
USPC .......................................... 600/437; 600/476
(58) Field of Classification Search
USPC .................. 600/407, 437, 473, 476
See application file for complete search history.

(56) References Cited

U.S. PATENT DOCUMENTS

| | | | |
|---|---|---|---|
| 5,348,002 A | 9/1994 | Caro | |
| 5,713,356 A | 2/1998 | Kruger | |
| 5,840,023 A | 11/1998 | Oraevsky et al. | |
| 5,977,538 A | 11/1999 | Unger et al. | |
| 5,999,836 A | 12/1999 | Nelson et al. | |
| 6,049,728 A | 4/2000 | Chou | |
| 6,102,857 A | 8/2000 | Kruger | |
| 6,216,540 B1 | 4/2001 | Nelson et al. | |
| 6,390,978 B1 | 5/2002 | Irion et al. | |
| 6,979,292 B2 | 12/2005 | Kanayama et al. | |
| 2003/0055308 A1 | 3/2003 | Friemel et al. | |
| 2003/0069491 A1 | 4/2003 | Kruger | |
| 2003/0097049 A1 | 5/2003 | Diab et al. | |
| 2003/0167002 A1 | 9/2003 | Nagar et al. | |
| 2004/0042006 A1 | 3/2004 | Chen et al. | |

FOREIGN PATENT DOCUMENTS

| | | |
|---|---|---|
| JP | 57-25835 | 2/1982 |
| JP | 3-165257 | 7/1991 |
| JP | 2001-507952 | 6/2001 |
| JP | 2004-613 | 1/2004 |
| JP | 2004-506467 | 3/2004 |
| WO | WO 02/15776 | 2/2002 |

*Primary Examiner* — Jonathan Cwern
(74) *Attorney, Agent, or Firm* — Oblon, Spivak, McClelland, Maier & Neustadt, L.L.P.

(57) ABSTRACT

A non-invasive subject-information imaging apparatus according to this invention includes a light generating unit which generates light containing a specific wavelength component, a light irradiation unit which radiates the generated light into a subject, a waveguide unit which guides the light from the light generating unit to the irradiation unit, a plurality of two-dimensionally arrayed electroacoustic transducer elements, a transmission/reception unit which transmits ultrasonic waves to the subject by driving the electroacoustic transducer elements, and generates a reception signal from electrical signals converted by electroacoustic transducer elements, and a signal processing unit which generates volume data of a living body function by processing a reception signal corresponding to acoustic waves generated in the subject by light irradiation, and generates volume data of a tissue morphology by processing a reception signal corresponding to echoes generated in the subject upon transmission of the ultrasonic waves.

26 Claims, 16 Drawing Sheets

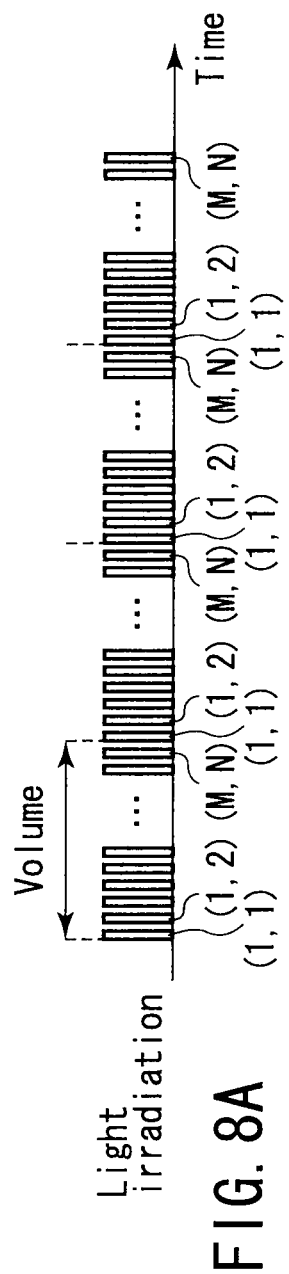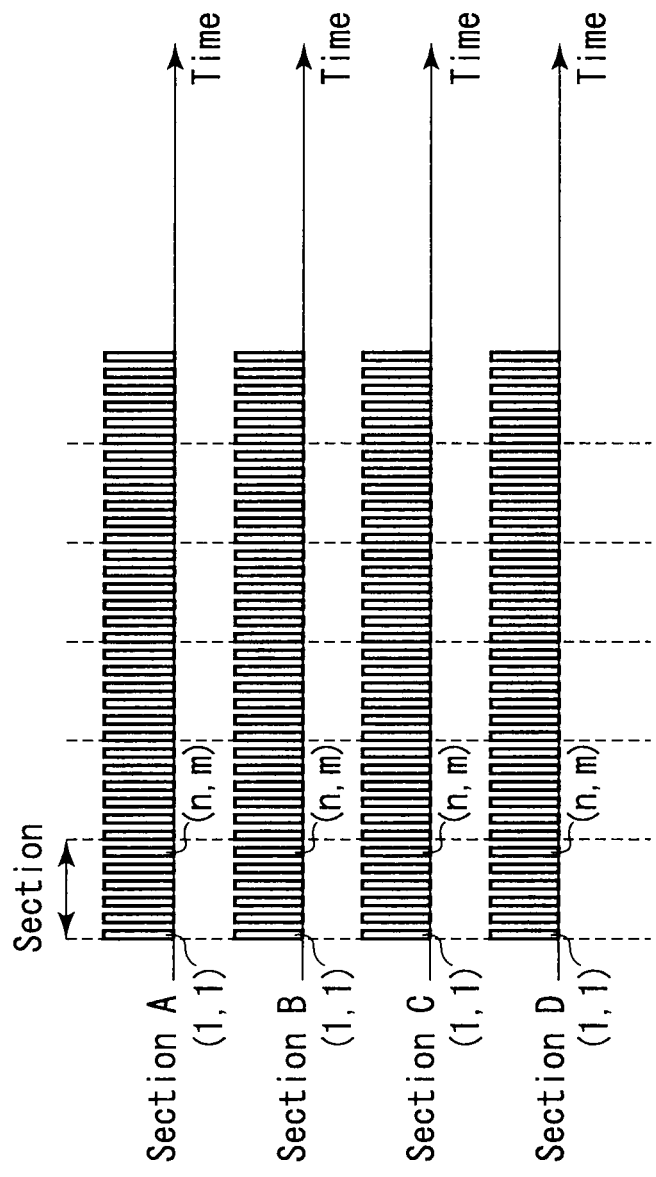
FIG. 8A
FIG. 8B

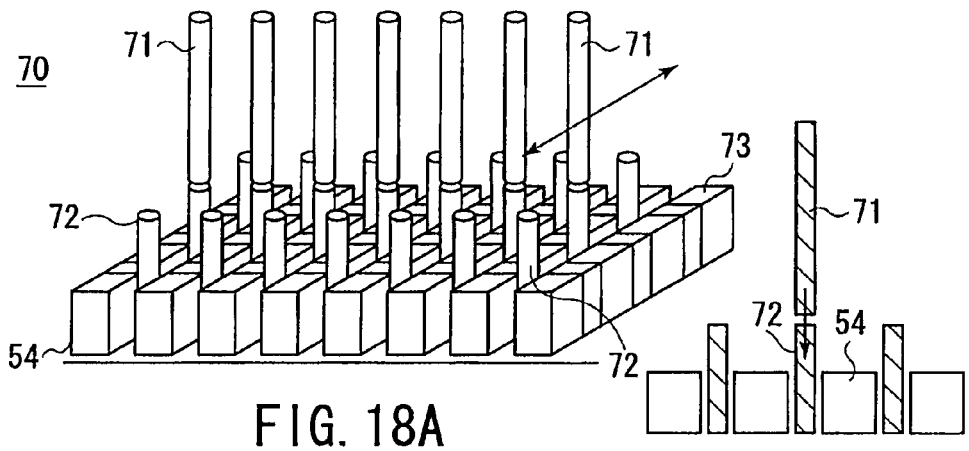
FIG. 18A
FIG. 18B
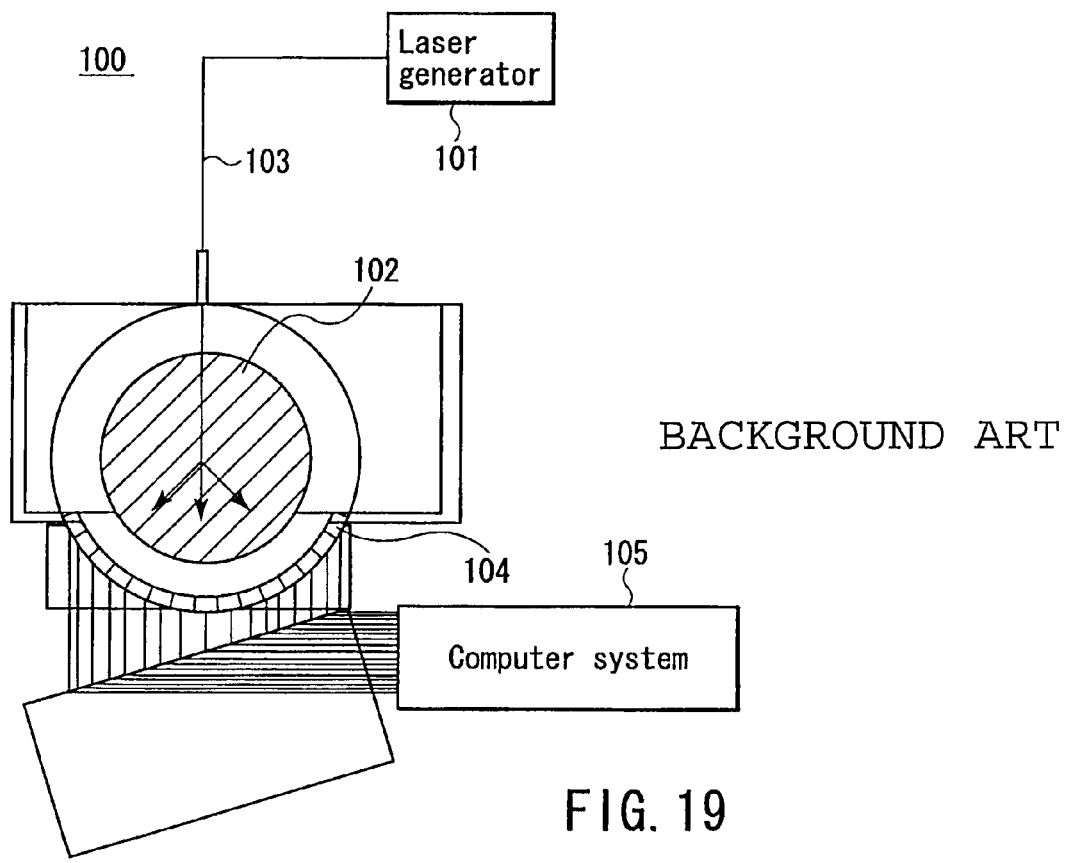
BACKGROUND ART
FIG. 19

NON-INVASIVE SUBJECT-INFORMATION IMAGING METHOD AND APPARATUS

CROSS-REFERENCE TO RELATED APPLICATIONS

This application is a continuation of U.S. application Ser. No. 10/812,884, filed Mar. 31, 2004, which is based upon and claims the benefit of priority from prior Japanese Patent Application No. 2004-30578, filed Feb. 6, 2004, the entire contents of which are incorporated herein by reference.

BACKGROUND OF THE INVENTION

1. Field of the Invention

The present invention relates to a non-invasive subject-information imaging method and apparatus for imaging living body anatomical, functional, and/or metabolic information of a subject to be examined by acquiring acoustic signals generated on the basis of the energy of light radiated into the subject and, more particularly, to a method and apparatus which acquire and superimpose two acoustic images, one generated from the energy of light radiated into a subject to be examined and the other is an ultrasound echo image generated from ultrasonic waves directed into the subject, and allow an operator to know the distribution of substance concentrations with respect to morphological features in the subject's tissue by superimposing the two images.

2. Description of the Related Art

A subject-information measuring method of measuring the concentration of a substance component contained in a body fluid such as blood or cell fluid in the subject or living body tissue has been performed in healthcare, determination on a therapeutic effect, and the like. In performing component analysis on a body fluid to measure the concentration of each component, the body fluid must be extracted from the subject by blood collection. This method therefore damages the skin of the subject, causing much pain to the subject. This also introduces the possibility of biohazard contamination to the subject and the operator.

With regard to such a conventional problem, a number of patents and journal articles describe non-invasive methods of acquiring information about analyte concentration in the tissue of human subjects. One of the methods is "photoacoustic spectroscopy". In the photoacoustic spectroscopy, the concentration of a specific substance, such as glucose or hemoglobin, contained in the blood of a subject is quantitatively measured by detecting the acoustic waves that are generated when the subject is irradiated with visible light, infrared light, or intermediate infrared light having a predetermined wavelength, and the specific substance absorbs the energy of the irradiated light. With regard to this, U.S. Pat. No. 5,348,002, EP9838904A1, EP0215776A1 describe methods for the non-invasive determination of substances in human tissue using photoacoustic measurements. The light may be visible light, infrared light, or intermediate infrared light.

In addition to glucose and hemoglobin described above, cholesterol, natural fat, bilirubin, collagen, and the like can be used as substances as targets for non-invasive subject-information measurement. Diagnosis of cutaneous cancer or breast cancer by the photoacoustic spectroscopy has recently proven its clinical usefulness. The photoacoustic spectroscopy uses the wavelength of light at which an optimal substance selected from these substances exhibits the highest absorption. In addition, it is increasingly expected that an image diagnosis method be invented, which provides a two-dimensional image representing the concentration distribution of these substance.

In a conventional non-invasive method of measuring glucose, the skin of the subject is irradiated with near-infrared light beams of different wavelengths. The glucose concentration is measured by arithmetically processing the acoustic waves obtained (see, for example, Jpn. Pat. Appln. KOKOKU Publication Nos. 3-47099 and 5-58735).

The conventional photoacoustic spectroscopy uses a microphone and a piezoelectric element made of lead zirconate titanate (PZT) ceramics, or the like, to detect acoustic waves (see, for example, Jpn. Pat. Appln. KOKAI Publication Nos. 10-189 and 11-235331).

In addition to hemoglobin and glucose, photoacoustic spectroscopy can be used to determine other analytes in human tissue such as cholesterol, natural fat, bilirubin, collagen, and the like. Diagnosis of cutaneous cancer or breast cancer based on the results of the photoacoustic spectroscopy has recently proven its clinical usefulness. The photoacoustic spectroscopy utilizes a suitable substance selected from these substances and light having a wavelength at the substance selected exhibits highest absorption. Further it is increasingly expected that a diagnosis method be invented, which provides a two-dimensional image representing the concentration distribution of these substances.

While photoacoustic spectroscopy is used to measure substance concentration in tissue, ultrasound images have been extensively used for determination of the presence of morphological features, such as cysts and lumps, in human organs. Combining the distribution of substances and the morphological features in human tissue leads to better diagnosis and improved healthcare as it provides better characterization of the tissue, more accurate diagnosis for malignancies, and better definition of regions of abnormal pathology to guide in surgical removal of these regions.

Breast cancer is a major source of mortality in females. Screening for and early diagnosis of breast cancer are of tremendous value in cutting mortality rate and in health care cost containment. Current methods involve manual examination of breast tissue for unusual lumps and routine mammography to look for suspicious lesions. If a mammogram is deemed suspicious, it is followed by ultrasound imaging, and surgical biopsy. These set of steps take considerable time before reaching a final conclusion.

Non-invasive optical techniques offer the opportunity for determining blood vessel distribution in tissue, thus locating a potential tumor by the presence of abnormal vascularization in a tissue region.

Non-invasive optical techniques include time resolved light propagation in tissue. Another method is the measurement of the change in modulation and phase angle as photon density wave propagate in the tissue. These are presented is several journal articles (B. Chance "Near-infrared images using continuous, phase-modulated, and pulsed light with quantitation of blood and blood oxygenation" in Advances in Optical Biopsy and Optical Mammography, R. Alfano ed, Annals of the New York Academy of Sciences 1998; Volume 838: pages 29-45; by S. Fantini et al "Frequency domain optical mammography: Edge effect corrections" Medical Physics 1996; Volume 23: pages 1-6, and by M. A. Franceschini et al "Frequency Domain techniques enhance optical mammography; initial clinical results" Proceedings of the National Academy of Sciences USA 1997; Volume 94: pages 6468-6473 (1997). These methods suffer from imprecision of image conversion and image distortions close to the edges of the body part, such as the breast.

Conventional imaging methods that include ultrasound, CAT scan, X-ray and MRI describe the morphology of the body part, in this case the breast without indicating the distribution of hemoglobin. Further, MRI and CAT scan require large expensive equipment that cannot be transformed easily.

A diagnostic method and apparatus that utilizes the morphological image and the distribution of substances in the morphological feature leads to better diagnosis.

Use of photoacoustic imaging to determine analyte distribution in breast tissue was described by A. A. Oraevsky et al "Laser opto-acoustic imaging of breast: Detection of cancer angiogenesis" SPIE Proceedings 1999; Volume 3597, pages: 352-363; and A. A. Oraevsky et al "Opto-acoustic imaging of blood for visualization and diagnostics of breast cancer" SPIE Proceedings 2002; Volume 4618, pages: 81-94. It is also described in U.S. Pat. No. 5,840,023 "Optoacoustic imaging for medical diagnosis", EP 01/10295 "Photoacoustic monitoring of blood oxygenation", and U.S. Pat. No. 6,309,352 B1 "Real Time optoacoustic monitoring of changes in tissue properties".

Oraevsky et al use photoacoustic imaging alone without combination with ultrasound imaging. They do not teach combination of photoacoustic and ultrasound images that are detected using positioned ultrasound transducers. The method leads to the possibility of distortion of the vascular image due to effect of the morphological features on tissue bulk modulus.

Other application of optical methods to generate an image of analyte distribution in tissue is described by Q. Zhu et al in "Combined ultrasound and optical tomography imaging" SPIE Proceedings 1999; Volume 3579, pages: 364-370; and Q. Zhu et al "Optical imaging as an adjunct to ultrasound in differentiating benign from malignant lesions" SPIE Proceedings 1999; Volume 3579: pages 532-539. Zhu et al uses ultrasound imaging to define the morphological features in tissue and then apply frequency domain imaging to determine vascularization, e.g., hemoglobin distribution. Optical fibers and photomultiplier tubes are used as detectors for the optical method and ultrasound transducers are used for ultrasound imaging with less optimum positioning between the vascularization and the morphological images. Zhu et al, however, do not teach combination of photoacoustic and ultrasound images that are detected using positioned ultrasound transducers.

Research has been conducted on imaging methods using the photoacoustic effect for diagnosing breast cancer (see, for example, Alexander A et al., "Laser optoacoustic imaging of breast cancer in vivo", Pros. SPIE, Vol. 4256, pp. 6-15, 2001). FIG. 19 illustrates a system 100 for acquiring photoacoustic image data, described in this reference. The system 100 is comprised of a laser generator 101, an optical fiber 103, an array of electroacoustic transducer elements 104 each having a concave surface, and a computer system 105. The laser generator 101 generates light pulses. The optical fiber 103 guides the light pulse to a breast 102 of a subject to be examined. The electroacoustic transducer elements 104 are placed facing the optical fiber 103. The computer system 105 controls transmission of optical pulses, acquires acoustic waves, and reconstructs an image. After the breast 102 is positioned between the optical fiber 103 and the array of electroacoustic transducer elements 104, the internal tissues in the breast 102 are irradiated with light (laser beam) from the optical fiber 103. The blood components in the internal tissues generate acoustic waves. The electroacoustic transducer elements 104 receive the acoustic waves.

In this method, the concentration of hemoglobin in blood, for example, can be measured with higher sensitivity than the concentration of any other substance components, by virtue of the photoacoustic effect based on a predetermined wavelength. Therefore, a photoacoustic image obtained from a tumor tissue such as a breast cancer in which the blood flow rate is higher than that in normal tissues can have higher detectability than an image obtained by an ultrasonic diagnosis apparatus, X-ray apparatus, MRI apparatus, or the like, which has conventionally been used. This is because vascularization, which is the number of blood vessels, and the blood flow rate are higher in the tumor tissue than in normal tissues, in order to accommodate the higher metabolic activity in the tumor. Increased vascularization occurs through generation of more blood vessels in the tumor and its surroundings. Generation of new blood vessels in tumors is known as angiogenesis.

The methods disclosed in the above references are designed to measure the concentration of a specific substance in a local region. However, none of these references teaches techniques of imaging concentration distributions.

The method described in above reference lacks operability. This is because, the optical fiber 103 and the array of electroacoustic transducer elements 104 opposite to each other, with the breast 102 being held between them. It is desirable to integrate the optical fiber 103 and the array of electroacoustic transducer elements 104, because air must be expelled, as much as possible, from the gap between the array and the subject, particularly when an image is reconstructed from the acoustic waves received from inside the subject.

In addition, image reconstruction using such acoustic waves (referred to as "photoacoustic imaging method" hereinafter) is performed only for a particular component such as hemoglobin. Hence, no signals can be obtained from any region that contains no such specific component. Therefore, when the photoacoustic imaging method is performed to examine the breast for cancer as described in non-patent reference 1, it is difficult to determine an accurate positional relationship between a tumor tissue and a healthy mammary gland tissue surrounding it.

There is therefore a need to develop a method and apparatus which diagnose disease states by combining imaging of morphological features and distribution of substance concentration within the features, while avoiding image distortion, incorporating a common body interface and common detector, for the imaging measurement and the substance distribution measurement. The method and the apparatus should lead to applying the same pressure, same air gaps, same interfaces to the imaging measurement and the substance distribution measurement.

BRIEF SUMMARY OF THE INVENTION

It is an object of the present invention to acquire living body function information about a volume of a subject to be examined, together with tissue morphology information about the same volume.

According to a first aspect of the present invention, there is provided a non-invasive subject-information imaging apparatus comprises a light generating unit which generates light containing a specific wavelength component, a light irradiation unit which radiates the light generated by the light generating unit into a subject to be examined, waveguide means for guiding the light generated by the light generating unit to the irradiation unit, a plurality of two-dimensionally arrayed electroacoustic transducer elements which convert acoustic waves from the subject into electrical signals, transmission means for transmitting ultrasonic waves to the subject by driving the plurality of electroacoustic transducer elements, reception means for generating a reception signal having reception directivity from the plurality of electrical signals converted by the plurality of electroacoustic transducer elements, and signal processing means for generating volume data about a living body function by processing a reception signal corresponding to acoustic waves generated in the subject by light radiated from the irradiation unit, and generating volume data about a tissue morphology by processing a reception signal corresponding to echoes generated in the subject upon transmission of the ultrasonic waves.

According to a second aspect of the present invention, there is provided a non-invasive subject-information imaging method comprising irradiating a subject to be examined with light containing a specific wavelength component from a plurality of two-dimensionally arranged light irradiation positions, causing a plurality of two-dimensionally arranged electroacoustic transducer elements to receive acoustic waves generated in the subject upon the irradiation of light, driving the plurality of electroacoustic transducer elements to transmit ultrasonic waves in a plurality of directions corresponding to the plurality of light irradiation positions, causing the plurality of electroacoustic transducer elements to receive echoes of the ultrasonic waves, generating volume data about a living body function of the subject on the basis of a reception signal corresponding to the acoustic waves, and generating volume data about a tissue morphology of the subject on the basis of a reception signal corresponding to the echoes.

Additional objects and advantages of the present invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention and, together with the general description given above and the detailed description of the preferred embodiments given below, serve to explain the principles of the invention.

FIGS. 8A and 8B are supplementary views for FIG. 7;

FIGS. 18A and 18B are views showing still another structure of the applicator in FIG. 1; and FIG. 19 is a view showing a conventional acquisition system for photoacoustic image data.

DETAILED DESCRIPTION OF THE INVENTION

An embodiment of the present invention will be described below with reference to the views of the accompanying drawing. A subject-information imaging apparatus according to this embodiment can image a hemoglobin distribution in the subject, which is mainly directed to diagnosis of breast cancer. More specifically, a plurality of electroacoustic transducer elements are two-dimensionally arranged at predetermined intervals in the vertical and horizontal directions, and the output ends of a plurality of optical fibers for light irradiation are arranged in the gaps between the electroacoustic transducer elements, thereby forming an applicator in which an irradiation unit is integrated with an electroacoustic conversion unit. By using this arrangement, volume data corresponding to a three-dimensional region representing a living body function is acquired by two-dimensional electroacoustic scanning based on light irradiation from the irradiation unit and detection of the resultant acoustic waves generated by the electroacoustic conversion unit. Volume data representing the tissue morphology of the same region is acquired by ultrasonic scanning based on the transmission of ultrasonic waves by the electroacoustic conversion unit and the detection of echoes.

Hereinafter, the sound waves generated by the photoacoustic scanning method will be referred to as "acoustic waves" and the sound waves transmitted/received in normal ultrasonic scanning will be referred to as "ultrasonic waves", thus discriminating them from each other.

Figure 1:
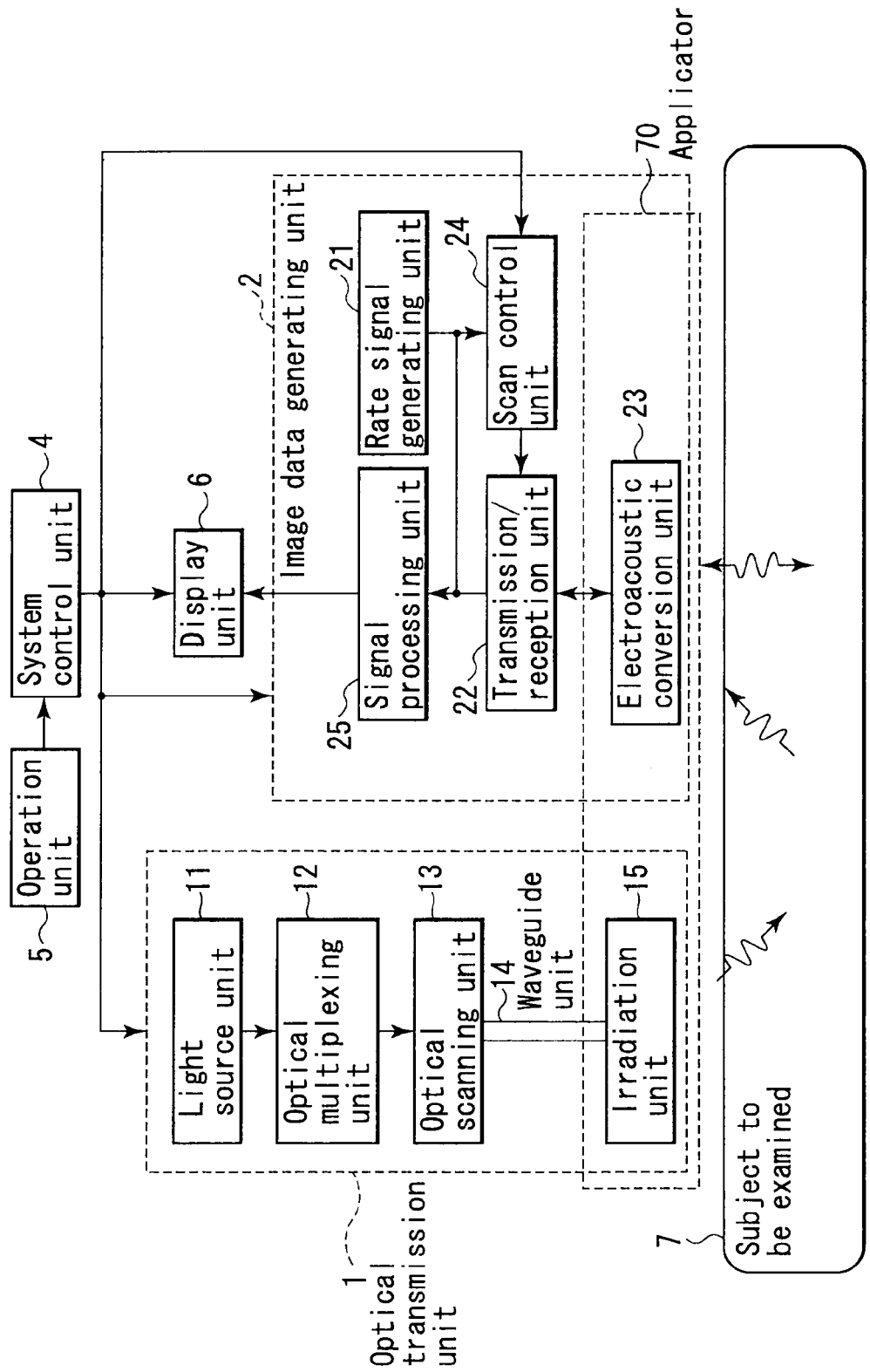
FIG. 1 is a block diagram showing the schematic arrangement of a non-invasive subject-information imaging apparatus according to an embodiment of the present invention.
Figure 2:
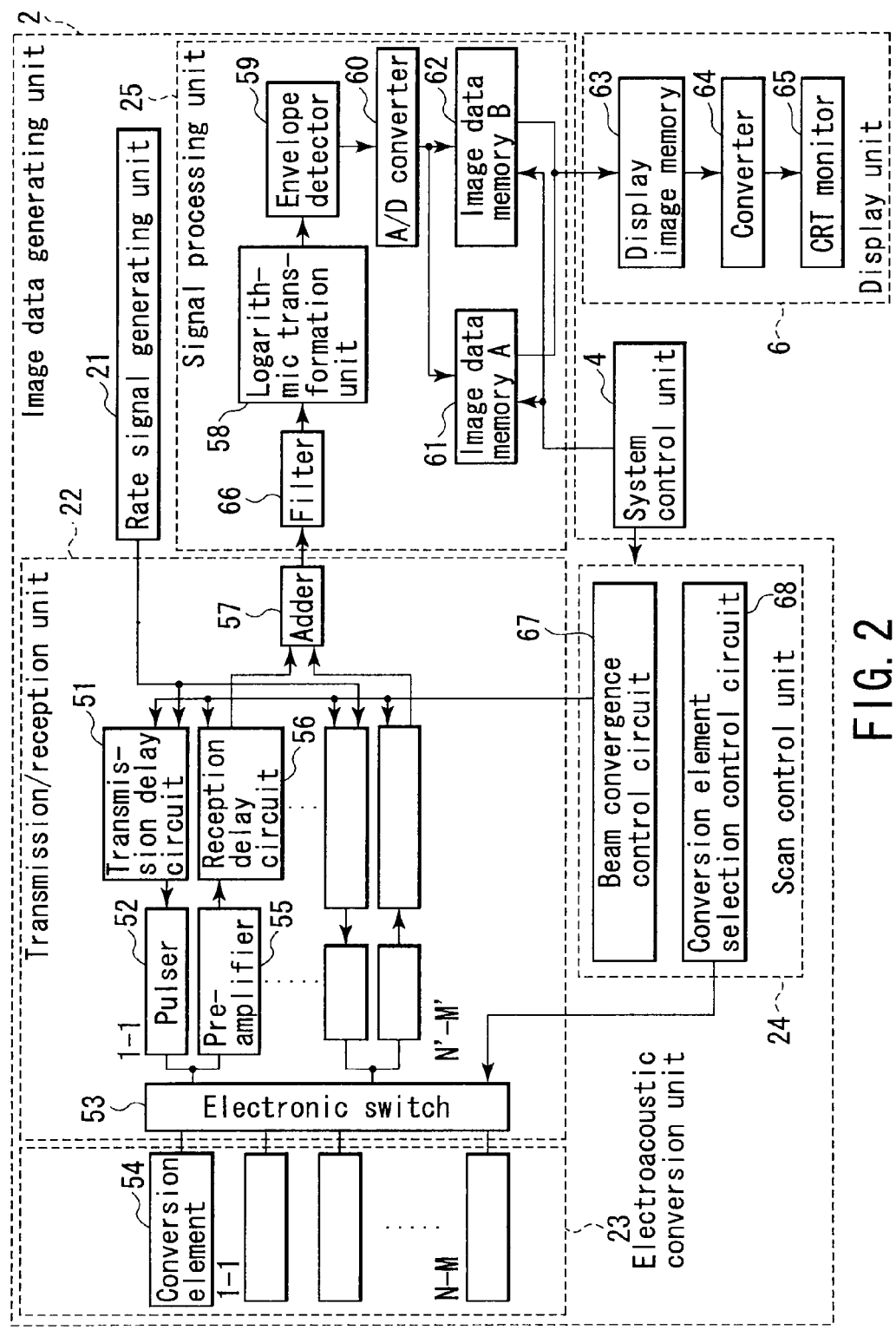
FIG. 2 is a block diagram of an image data generating unit in FIG. 1.
Figure 3:
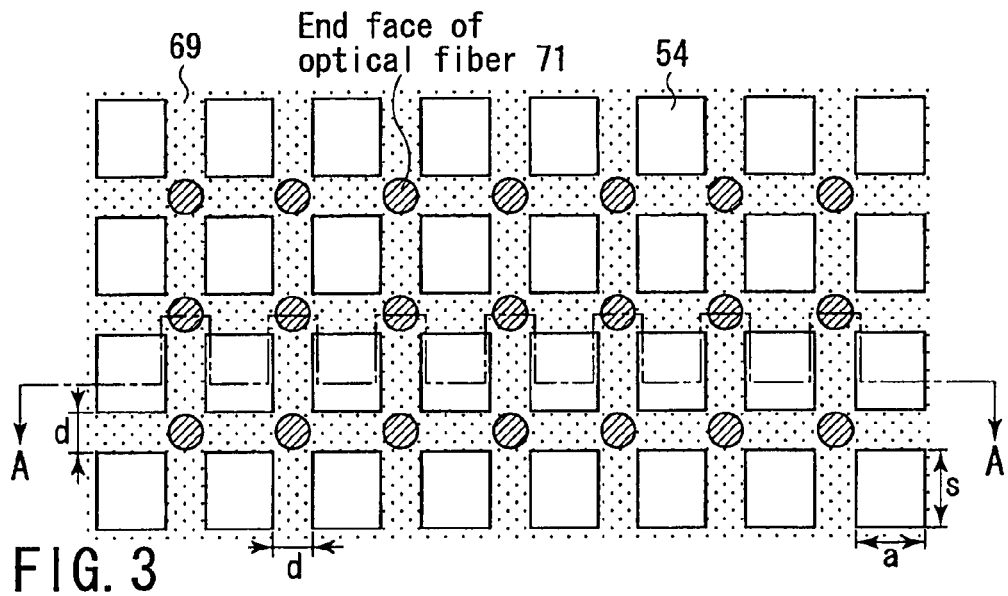
FIG. 3 is a schematic plan view showing the array structure of an irradiation unit and electroacoustic conversion unit in an applicator in FIG. 1.
Figure 4A:
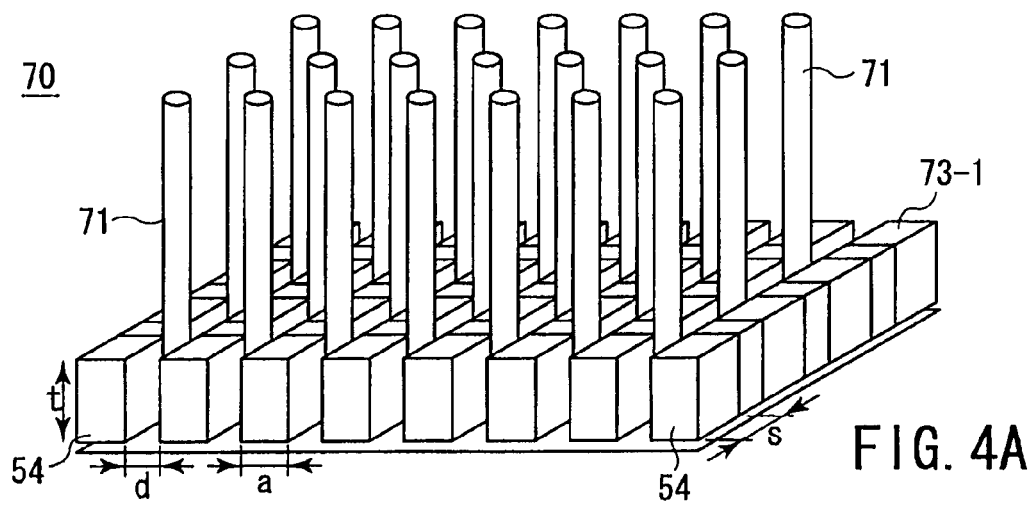
FIGS. 4A and 4B are a perspective view and sectional view, respectively, showing the array structure of the irradiation unit and electroacoustic conversion unit in the applicator in FIG. 1.
Figure 4B:
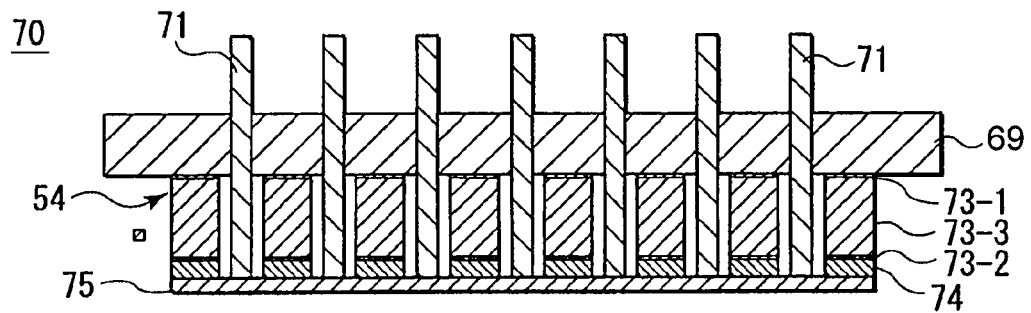
Figure 5:
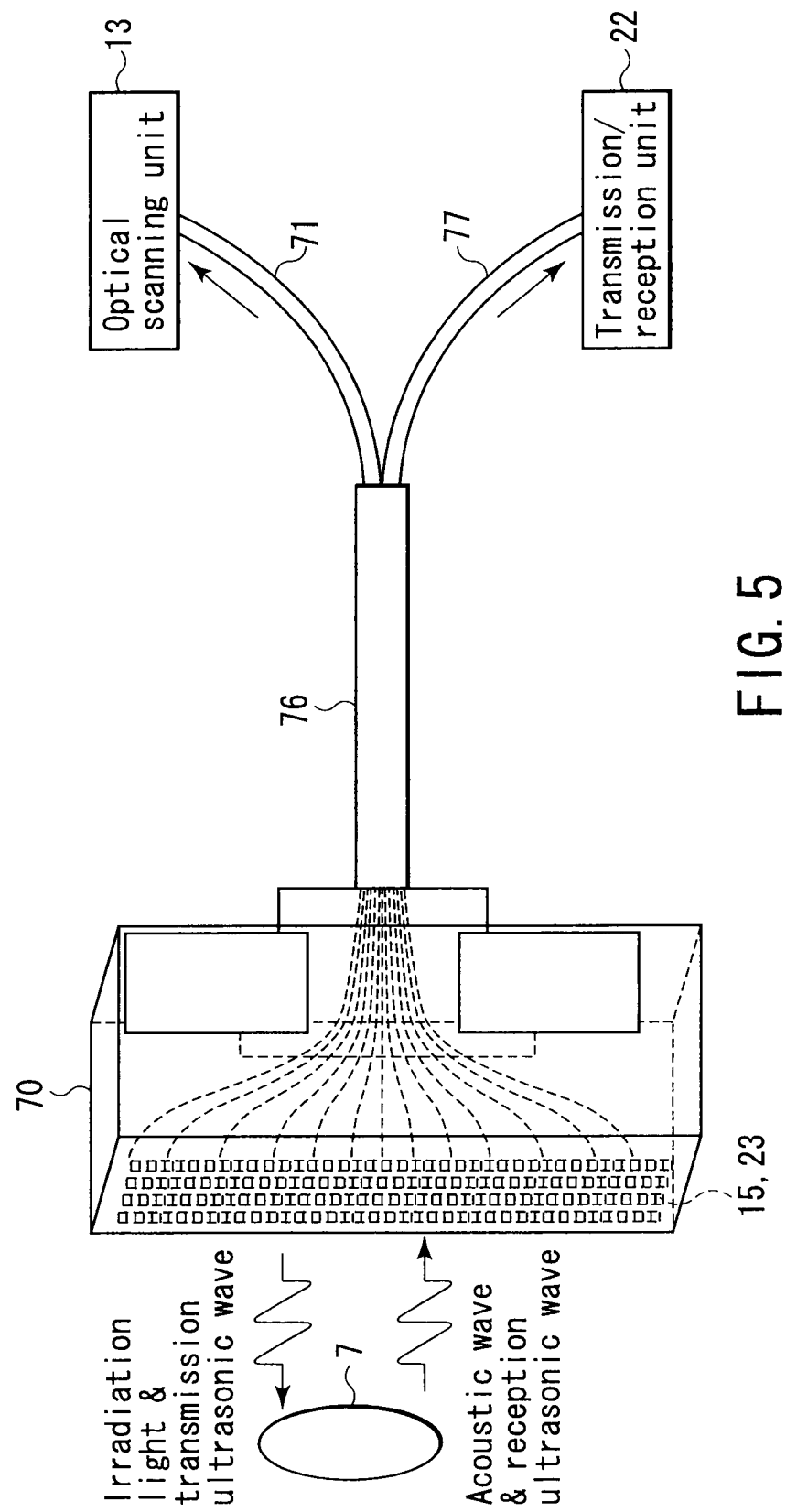
FIG. 5 is a view showing the outer appearance of the applicator in FIG. 1.

FIG. 1 is a block diagram showing the schematic arrangement of the overall non-invasive subject-information imaging apparatus. FIG. 2 is a block diagram showing an image data generating unit 2 in FIG. 1. FIG. 3 is a schematic plan view showing the array structure of the irradiation unit and electroacoustic conversion unit in the applicator. FIGS. 4A and 4B are a perspective view and sectional view showing the array structure of the irradiation unit and electroacoustic conversion unit in the applicator in FIG. 1. FIG. 5 is a view showing the outer appearance of the applicator in FIG. 1.

The non-invasive subject-information imaging apparatus of this embodiment is comprised of an optical transmission unit 1, image data generating unit 2, display unit 6, operation unit 5, and system control unit 4. The optical transmission unit 1 emits light having a specific wavelength. The image data generating unit 2 generates volume data about a living body function and the function image data of an arbitrary slice by receiving the acoustic waves generated in a subject 7 upon irradiation of the subject with the light from the optical transmission unit 1. The image data generating unit 2 also generates volume data about the tissue morphology of the subject and the morphological image data of an arbitrary slice by receiving the echoes of the ultrasonic waves transmitted to the subject 7. The display unit 6 displays the function image data and morphological image data. By using the operation unit 5, the operator inputs patient information and imaging conditions for the apparatus. The system control unit 4 systematically controls the respective units.

The optical transmission unit 1 has a light source unit 11, optical multiplexing unit 12, multi-channel waveguide unit 14, optical scanning unit 13, and irradiation unit 15. The light source unit 11 has a plurality of light sources of different wavelengths. The optical multiplexing unit 12 multiplexes light beams having different wavelengths on the same optical axis. The multi-channel waveguide unit 14 guides this light onto the skin of the subject 7. The optical scanning unit 13 scans the subject 7, while switching channels to be used in the waveguide unit 14. The irradiation unit 15 irradiates the subject 7 with the light applied through the waveguide unit 14.

The light source unit 11 has a plurality of light sources, which generate light beams of different wavelengths. Each light source is a light-emitting element such as a semiconductor laser (LD), light-emitting diode (LED), solid-state laser or gas laser, which generates a specific wavelength component or monochromatic light containing it. To measure the hemoglobin concentration in the subject 7, either an Nd:YAG laser, a kind of solid-state laser, having a wavelength of about 1,000 nm or an He—Ne gas laser, a kind of gas laser, having a wavelength of 633 nm is used to generate a laser beam having a pulse width of about 10 nsec. Although hemoglobin in a living body varies in optical absorption, depending on its type (oxyhemoglobin, deoxyhemoglobin, methemoglobin, carbaminohemoglobin, or the like), it generally absorbs light in the range of 600 nm to 1,000 nm.

A compact light-emitting element, such as an LD or LED, may be used, which is made of InGaAlP for an emission wavelength of about 550 to 650 nm; GaAlAs for an emission wavelength of about 650 to 900 nm; or InGaAs or InGaAsP for an emission wavelength of about 900 to 2,300 nm. Recently, a light-emitting element made of InGaN, which emits light with a wavelength of 550 nm or less, has come into use. Alternatively, an OPO (Optical Parametrical Oscillator) laser, which is a tunable laser using nonlinear optical crystal, may be used.

The optical multiplexing unit 12 is designed to multiplex light beams with different wavelengths emitted from a plurality of light sources on the same optical axis. A collimator lens converts the light beams into parallel light beams. A right-angled prism or dichroic mirror aligns the optical axes of the light beams. The collimator lens and the prism or mirror constitute a relatively compact multiplexing optical system. The system may be replaced by a commercially available multiple multiplexer/demultiplexer that has been developed for optical communication. If the light source unit 11 is the above-mentioned OPO laser that can continuously change wavelength, the optical multiplexing unit 12 need not be used.

The waveguide unit 14 guides the light output from the optical multiplexing unit 12 to the subject 7. An optical fiber or optical thin film waveguide is utilized for efficient optical propagation. Instead, free space propagation can also be employed. In the first embodiment, the waveguide unit 14 is comprised of a plurality of optical fibers 71. A predetermined one of these optical fibers 71 is selected, and the subject 7 is irradiated with light from the selected optical fiber 71.

The optical scanning unit 13 optically scans the subject 7 by sequentially selecting the plurality of optical fibers 71 arrayed in the waveguide unit 14.

The irradiation unit 15 is constituted by the output ends of the optical fibers 71. The irradiation unit 15 constitutes an applicator 70, together with an electroacoustic conversion unit 23. The output ends of the optical fibers 71 constituting the irradiation unit 15 are two-dimensionally arrayed in an M×N matrix. A plurality of conversion elements 54 constituting the electroacoustic conversion unit 23 are two-dimensionally arrayed in an (M+1)×(N+1) matrix. Note that the output ends of the optical fibers 71 constitute a flat surface, convex surface, or concave surface, together with the conversion elements 54 constituting the electroacoustic conversion unit 23. Assume that in this case, they constitute a flat surface.

The image data generating unit 2 of the non-invasive subject-information imaging apparatus includes an electroacoustic conversion unit 23, transmission/reception unit 22, scan control unit 24, rate signal generating unit 21, and signal processing unit 25. The electroacoustic conversion unit 23 converts acoustic and electrical signals. The transmission/reception unit 22 selectively drives the electroacoustic conversion unit 23, and generates a reception signal having reception directivity by delaying transmission/reception signals by predetermined time and performing phased addition. The scan control unit 24 controls the selective operation of the electroacoustic conversion unit 23 and the delay time given by the transmission/reception unit 22. The rate signal generating unit 21 outputs a rate pulse for setting the repeating period of transmission ultrasonic waves to be radiated into the subject 7. The signal processing unit 25 performs various processes on the signals received from the transmission/reception unit 22.

The electroacoustic conversion unit 23 includes a plurality of small conversion elements 54 which are two-dimensionally arrayed. The electroacoustic conversion unit 23 receives both the acoustic waves generated in the subject upon irradiation with light from the irradiation unit 15 and the echoes of the ultrasonic waves transmitted from the electroacoustic conversion unit 23. The conversion element 54 can convert an electrical driving pulse into a transmission ultrasonic wave at the time of transmission. The conversion elements 54 can also convert an acoustic wave or echo into an electrical signal at the time of reception. The electroacoustic conversion unit 23, generally called an "ultrasonic probe", has a compact and light body. The electroacoustic conversion unit 23 is connected to the transmission/reception unit 22 (to be described later) through a multi-channel cable. The electroacoustic conversion unit 23 may be a sector scan unit, linear unit, or convex scan unit, depending on which region should be diagnosed. In this embodiment, the unit 23 is a linear scan unit.

As FIG. 2 shows, the transmission/reception unit 22 includes transmission delay circuits 51, pulsers 52, electronic switch 53, preamplifiers 55, reception delay circuits 56, and adder 57. The transmission delay circuits 51 are designed to set the convergence distances of transmission ultrasonic waves at the time of transmission. The circuits 51 impart corresponding timings to the rate pulse output from the rate signal generating unit 21, and supplies the resultant pulses to the pulsers 52. The pulsers 52 are driving circuits which generate high-voltage pulses for driving the conversion elements 54. The pulsers 52 generate impulses having peak values of several hundred volts by using output signals from the transmission delay circuits 51 as trigger signals.

The electronic switch 53 selects all the conversion elements 54 constituting the electroacoustic conversion unit 23 or some adjacent conversion elements 54 at the time of transmission in ultrasonic scanning. At the time of reception of acoustic waves or echoes in photoacoustic scanning or ultrasonic scanning, the electronic switch 53 selects a predetermined number of conversion elements 54. The electronic switch 53 then supplies the electrical signals obtained by the conversion elements 54 to the preamplifiers 55. The preamplifiers 55 amplify the small reception signals received by the conversion elements 54 that have been selected by the electronic switch 53. This ensures sufficient S/N.

The reception delay circuits 56 give delay times to the acoustic waves or the electrical signals of the echoes obtained from the conversion elements 54 selected by the electronic switch 53 to generate a convergent reception beam upon matching the phases of the acoustic waves or echoes generating from a predetermined direction. The adder 57 combines the delayed electrical signals from a plurality of channels into one reception signal. Owing to this addition, phased addition of the reception signals from a predetermined depth is performed, thereby setting a reception conversion point.

The rate signal generating unit 21 generates clock pulses for setting the timing of transmitting ultrasonic pulses with a predetermined repetition frequency. The repetition frequency depends on the depth of field of an image. In this embodiment, this frequency is set to 4 kHz to 8 kHz.

The scan control unit 24 includes a conversion element selection control circuit 68 and beam convergence control circuit 67. The selection control circuit 68 supplies to the electronic switch 53 the position information about a predetermined number of conversion elements 54 that the electronic switch 53 selects at the time of transmission. The conversion element selection control circuit 68 also supplies to the electronic switch 53 the information about a predetermined number of conversion elements 54 selected at the time of reception. The beam convergence control circuit 67 supplies delay time information, from which a predetermined number of conversion elements 54 will form a transmission convergence point and a reception convergence point, to the transmission delay circuit 51 and reception delay circuit 56.

The signal processing unit 25 includes a filter 66, logarithmic transformation unit 58, envelope detector 59, A/D convertor 60, image data memory A 61, and image data memory B 62. The filter 66 removes unnecessary noise from an output from the adder 57 of the transmission/reception unit 22. The logarithmic transformation unit 58 logarithmically transforms the amplitude of the signal output from the filter 66, relatively enhancing this weak signal. Signals from the subject 7 generally have amplitude in a wide dynamic range of 80 dB or more. To display them on a general CRT monitor having a dynamic range of about 23 dB, amplitude compression must be carried out to enhance the weak signal.

The filter 66 has bandpass characteristics and has a mode of extracting the fundamental wave of a reception signal and a mode of extracting harmonic components. The envelope detector 59 detects the envelope of a reception signal logarithmically transformed. The A/D convertor 60 A/D converts the output signal from the envelope detector 59 into volume data.

This volume data includes two kinds of data, i.e., volume data which is generated on the basis of acoustic waves in photoacoustic scanning and represents a living body function and volume data which is generated on the basis of ultrasonic echoes transmitted to the subject 7 and represents tissue morphology. The image data memory A 61 is a storage circuit that stores the former living body function volume data. The image data memory B 62 is a storage circuit that stores the latter tissue morphology volume data. The data of an arbitrary slice is read out from the image data memory A 61 under the control of the system control unit 4. In this reading operation, the data is spatially interpolated to generate the living body function image data of the slice. The data of the same slice is read out from the image data memory B 62 under the control of the system control unit 4. In this reading operation, the data is spatially interpolated to generate the tissue morphology image data of the slice.

The display unit 6 includes a display image memory 63, convertor 64, and CRT monitor 65. The display image memory 63 is a buffer memory that temporarily stores image data to be displayed on the CRT monitor 65. The living body function image data read out from the image data memory A 61 and the tissue morphology image data read out from the image data memory B 62 are combined in the display image memory 63 into one frame. The convertor 64 performs D/A conversion and TV format conversion on the combined image data read out from the display image memory 63. The CRT monitor 65 displays the output from the convertor 64. The operation unit 5 has a keyboard, trackball, mouse, and the like, all mounted on the operation panel. The operation unit 5 is used by the operator of this apparatus to input necessary information such as subject information, imaging conditions for the apparatus, and a slice to be displayed.

The system control unit 4 has a CPU (not shown) and storage circuit (not shown). The unit 4 systematically controls, for example, the optical transmission unit 1, image data generating unit 2, and display unit 6, in accordance with command signals supplied from the operation unit 5. The unit 4 controls the entire system, too. The input command signals sent through the operation unit 5 are stored in the CPU provided in the system control unit 4.

The applicator 70 obtained by integrating the irradiation unit 15 and electroacoustic conversion unit 23 will be described with reference to FIGS. 3 to 4B. FIG. 4B is a sectional view taken along a line A-A of the applicator 70 in FIG. 3. Each conversion element 54 is constituted by a piezoelectric element 73-3 and electrodes 73-1 and 73-2 which are formed on the upper and lower surfaces of the piezoelectric element 73-3, respectively, to supply a driving signal and extract an electrical signal. An acoustic matching layer 74 is formed on the electrode 73-2 to accomplish efficient transmission/reception of ultrasonic waves. The surface of the acoustic matching layer 74 is covered with a protective film 75.

Each conversion element 54 has a length s, thickness t, and width a. The conversion elements 54 are two-dimensionally arranged at predetermined intervals d in the vertical and horizontal directions on a support 69. The optical fibers 71 are two-dimensionally laid in the gaps between the conversion elements 54 such that each optical fiber 71 is surrounded by four adjacent conversion elements 54.

FIG. 5 is a view showing the outer appearance of the applicator 70. The electroacoustic conversion unit 23 and irradiation unit 15 arranged at the distal end of the applicator 70 come into contact with the surface of the subject 7 to irradiate the subject with irradiation light, receive acoustic waves, and transmit/receive ultrasonic waves. The optical fibers 71 coupled to the irradiation unit 15 and coaxial cables 77 connected to electrodes 73 of the conversion elements 54 are bundled in a sheath 76. End portions of the optical fibers 71 are connected to the optical scanning unit 13, and the other end portions of the coaxial cables 77 are connected to the transmission/reception unit 22 of the image data generating unit 2.

FIGS. 6A, 6B, 7, and 8A show a basic photoacoustic scanning sequence in this embodiment. For the sake of convenience, assume that the optical fibers 71 are arranged in an M×N matrix, and the central positions of the respective end faces will be represented as (1, 1), (1, 2), . . . , (M, N) in the array order. The operator operates the operation unit 5 to set necessary imaging conditions for photoacoustic scanning. The imaging conditions include various specifications of the applicator 70, in addition to a frame count, field depth, rate frequency, and type of the image display method. At the same time, the operator also sets conditions concerning a light source, such as the wavelength of light used for photoacoustic scanning. The imaging conditions thus set are stored in a storage circuit (not shown) in the system control unit 4.

When setting of the above imaging conditions is completed, the operator sets the applicator 70 at a predetermined position on the subject 7, and then operates the operating unit 5 to input a command to start acquisition of photoacoustic image data in photoacoustic scanning.

Upon receipt of the command to start acquisition of photoacoustic image data, the system control unit 4 reads out the conditions set for the light source from the internal storage circuit. In accordance with the set conditions, the light source unit 11 selects, for example, an Nd.YAG laser, which emits monochromatic light having a wavelength of 1,000 nm. The mono-chromatic light generated by the light source unit 11 is sent to the optical scanning unit 13 via the optical multiplexing unit 12.

Figure 7:
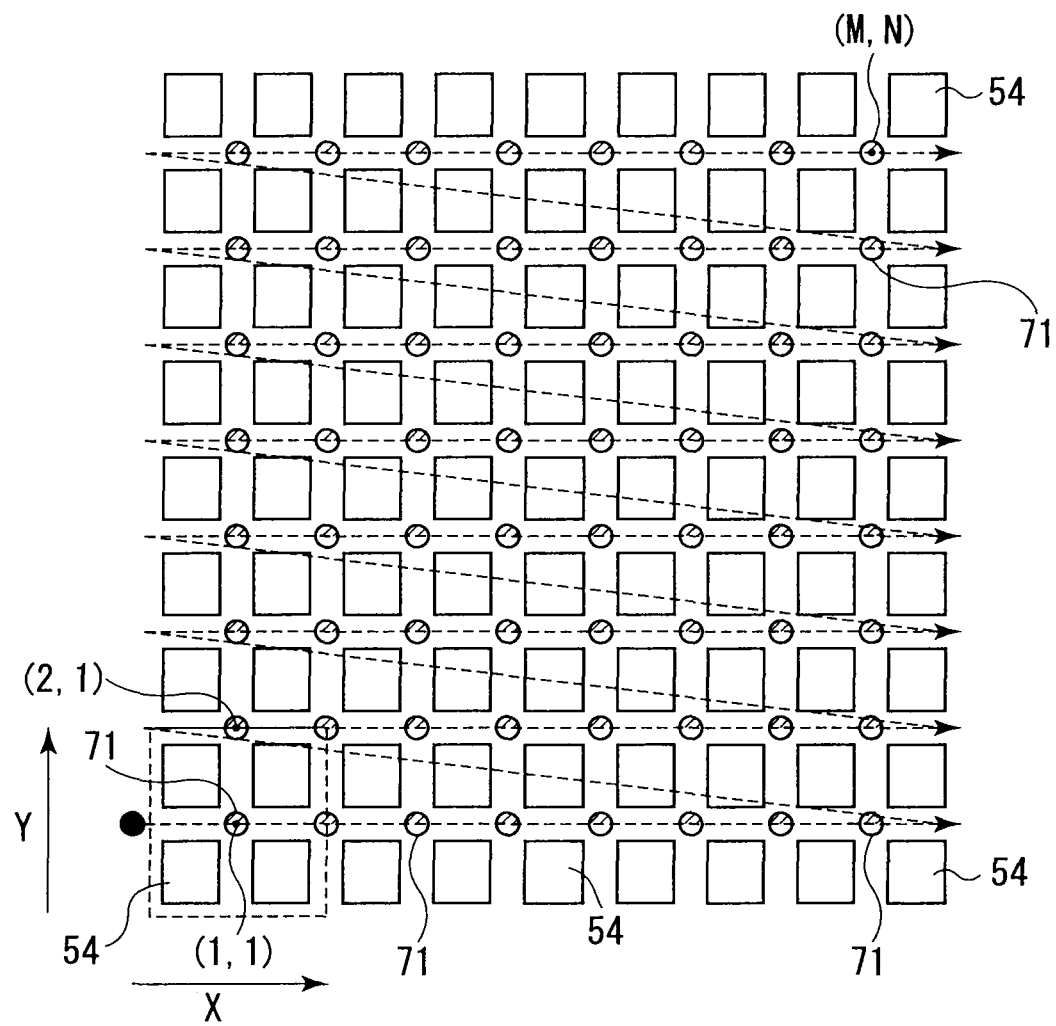
FIG. 7 is a view showing sequential photoacoustic scanning corresponding to FIGS. 6A and 6B.

As shown in FIGS. 7 and 8A, the optical scanning unit 13 selects the optical fibers 71 one by one at predetermined intervals in the array order. The selected fiber guides the light to the irradiation unit 15 of the applicator 70. The applicator 70 irradiates the subject 7 with light from the distal end portion of the irradiation unit 15. In this case, the monochromatic light radiated from the optical fiber 71 is applied almost perpendicular to that surface part of the subject 7 which is in contact with the applicator 70, as indicated by the arrow in FIG. 6A. That is, the light is applied in a direction perpendicular to the flat surface of the two-dimensional array of the optical fibers 71 and conversion elements 54.

The hemoglobin in the blood of the subject 7 absorbs the energy of the monochromatic light and then generates heat due to molecular collision. The thermal expansion of the heated hemoglobin induces a pressure change to generate an acoustic wave. The acoustic wave generated at this time is a pulse wave that has a broadband spectrum component of 100 kHz to 2 MHz. According to the photoacoustic effect, the wavelength of light to be applied to the subject is determined from the substance that should be measured, and the content of substance can be quantified from the magnitude of acoustic waves obtained by irradiating the subject with light having the wavelength determined. Thus, the amount of hemoglobin in the irradiation region of the subject 7 can be measured by irradiating the subject 7 with the monochromatic light emitted from the above Nd.YAG laser and having a wavelength of 1,000 nm.

Figure 6A:
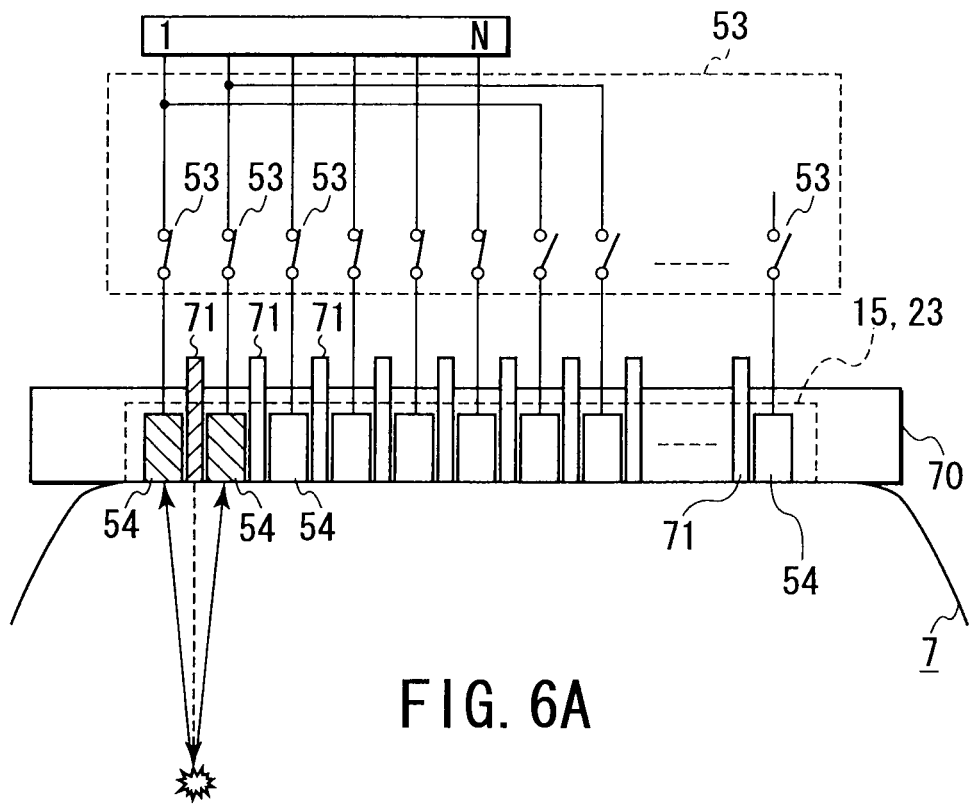
FIGS. 6A and 6B are views showing light irradiation and acoustic wave detection by four neighboring elements.
Figure 6B:
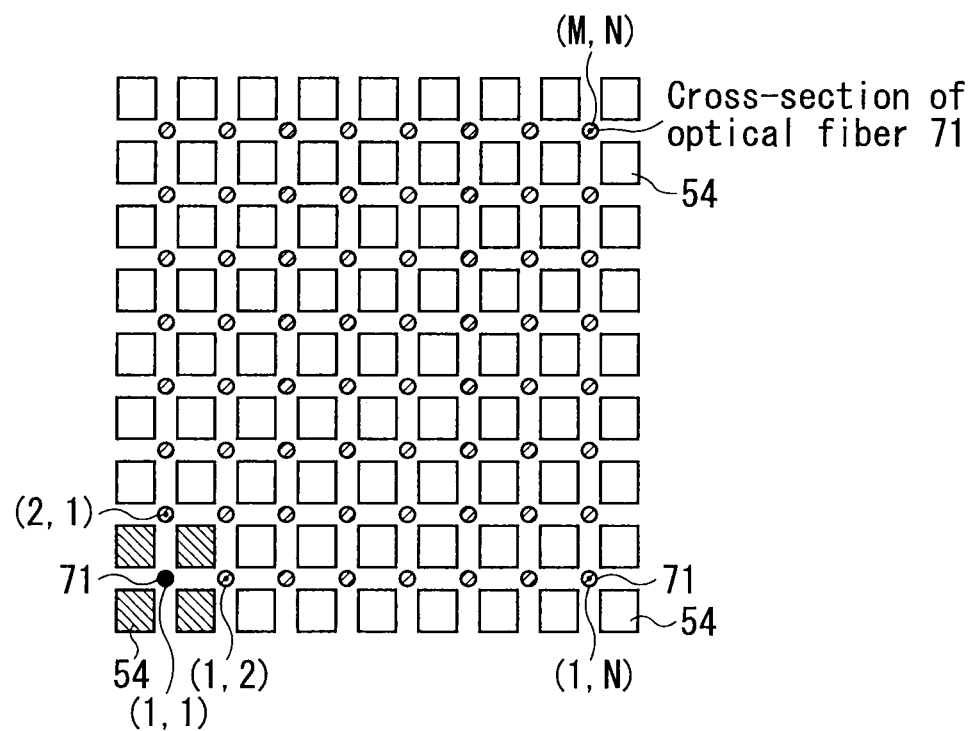
Figure 9A:
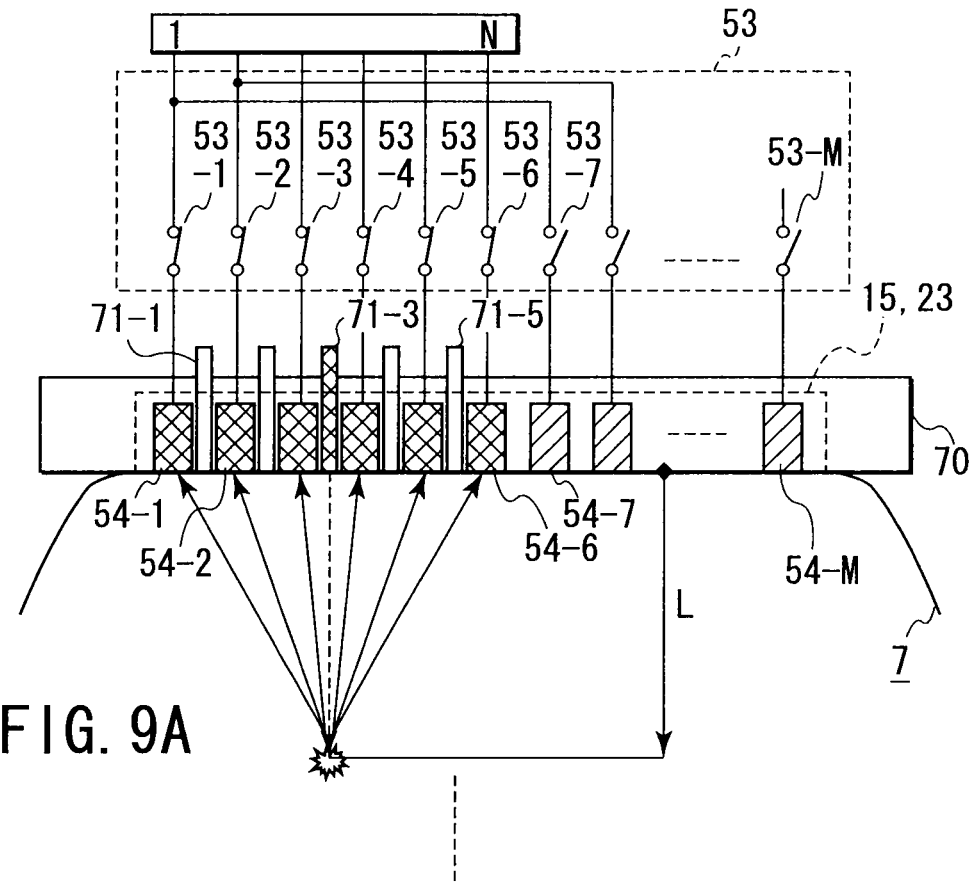
FIGS. 9A and 9B are views showing light irradiation and photoacoustic wave detection by 36 neighboring elements in this embodiment.
Figure 9B:
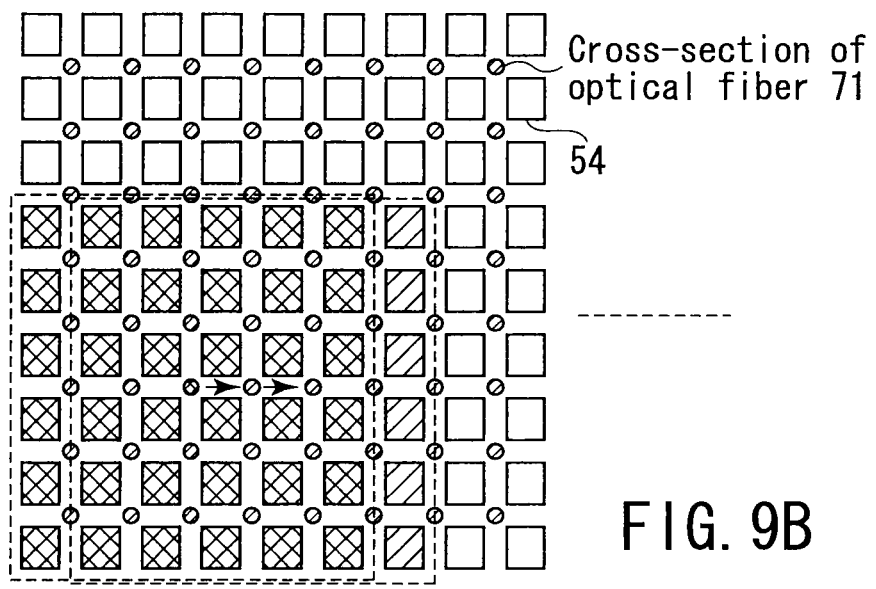

The acoustic waves generated by light irradiation are detected by a predetermined number of conversion elements 54 arranged near the irradiation position. For example, as shown in FIG. 6B, the acoustic waves are detected by the four conversion elements 54 around the light irradiation position. The number of conversion elements which simultaneously detect acoustic waves is not limited to four. For example, as shown in FIGS. 9A and 9B, optical fiber 71-3 is selected from a plurality of optical fibers (e.g., 71-1 and 71-5) to irradiate the subject with light and the resulting acoustic waves are detected by 6×6 conversion elements 54-1 through 54-6 (corresponding to switches 53-1 through 53-6) around the light irradiation position. In this example, conversion elements 54-7 through 54-M (corresponding to switches 53-7 through 53-M) are not used to detect the acoustic waves.

In practice, with respect to a blood vessel area in a region a distance L away from the subject contact surface of the applicator 70, the system control unit 4 supplies selection information for the conversion elements 54 in the scanning information stored in advance in the storage circuit to the conversion element selection control circuit 68 of the scan control unit 24, and also supplies delay time information concerning the convergence point distance setting at the time of reception to the beam convergence control circuit 67 of the scan control unit 24.

The electronic switch 53 selects the above four conversion elements from the conversion elements 54 of the applicator 70 in accordance with a control signal from the conversion element selection control circuit 68. In accordance with a control signal from the beam convergence control circuit 67, the reception delay circuit 56 gives the respective electrical signals obtained by the four conversion elements 54 delay times necessary to make the reception convergence point pass through the light irradiation position and be set at a position located on a straight line perpendicular to the flat surface of the two-dimensional array of the optical fibers 71 and the conversion elements 54 and spaced apart from the surfaces of the optical fibers 71 and conversion elements 54 by a predetermined depth.

That is, the selection control circuit 68 turns on four adjacent electronic switches 53 around the light irradiation position in accordance with the selection information that is supplied for the conversion elements 54 from the system control unit 4. The four conversion elements 54 around the optical fiber 71 selected/used at the time of light irradiation are selected as conversion elements 54 for reception. The conversion elements 54 convert the acoustic waves generated inside the subject 7 into electrical signals. These signals are supplied to the preamplifier 55 via the electronic switch 53. The preamplifier 55 amplifies the signals to a predetermined amplitude. The amplified signals are then input to the reception delay circuit 56.

Of the reception delay circuits 56 constituted by K channels, the kth reception delay circuit 56 delays the reception signal supplied from the kth conversion element 54 by delay time τ(k) given by:

$$\tau(k) = d^2(K-1)^2 - (2k-K-1)^2/8\, CFo \quad (1)$$

where d is the interval of the conversion elements 54, C is the acoustic wave propagation speed (about 1,500 m/sec) in the subject 7, Fo is the reception convergence point distance. If Fo=L, the delay times are imparted to the signals generated by the conversion elements 54. The adder 57 adds the resultant signals. This makes it possible to add/combine the signals while matching the phases of the acoustic waves generated at the distance L.

The period of time between the time the subject 7 is irradiated with light and the time the conversion element 54 receives the acoustic wave is proportional to the distance L. Therefore, a so-called dynamic convergence method can be used, which increases the reception convergence point distance Fo given by equation (1) at the time of the reception of acoustic waves. The acoustic waves generated by light irradiation using the selected optical fiber 71 can be received in a converged state regardless of the depth (distance). Therefore, photoacoustic volume data of high sensitivity and high spatial resolution can be generated from these reception signals.

The filter 66 of the signal processing unit 25 removes noise components from the electrical signals generated by the conversion elements 54 and combined by the adder 57 as a reception signal having directivity. The logarithmic transformation unit 58 and envelope detector 59 then perform amplitude compression and detection of this signal. The A/D convertor 60 converts the signal into a digital signal. The digital signal is stored, as photoacoustic image data, into the image data memory A 61.

A series of the above light irradiation and acoustic wave detection is sequentially repeated while the light irradiation position is moved. Light irradiation and acoustic wave detection are repeated M×N times. As a result, photoacoustic scanning for one volume is completed. This photoacoustic scanning for one volume is repeated.

Figure 10:
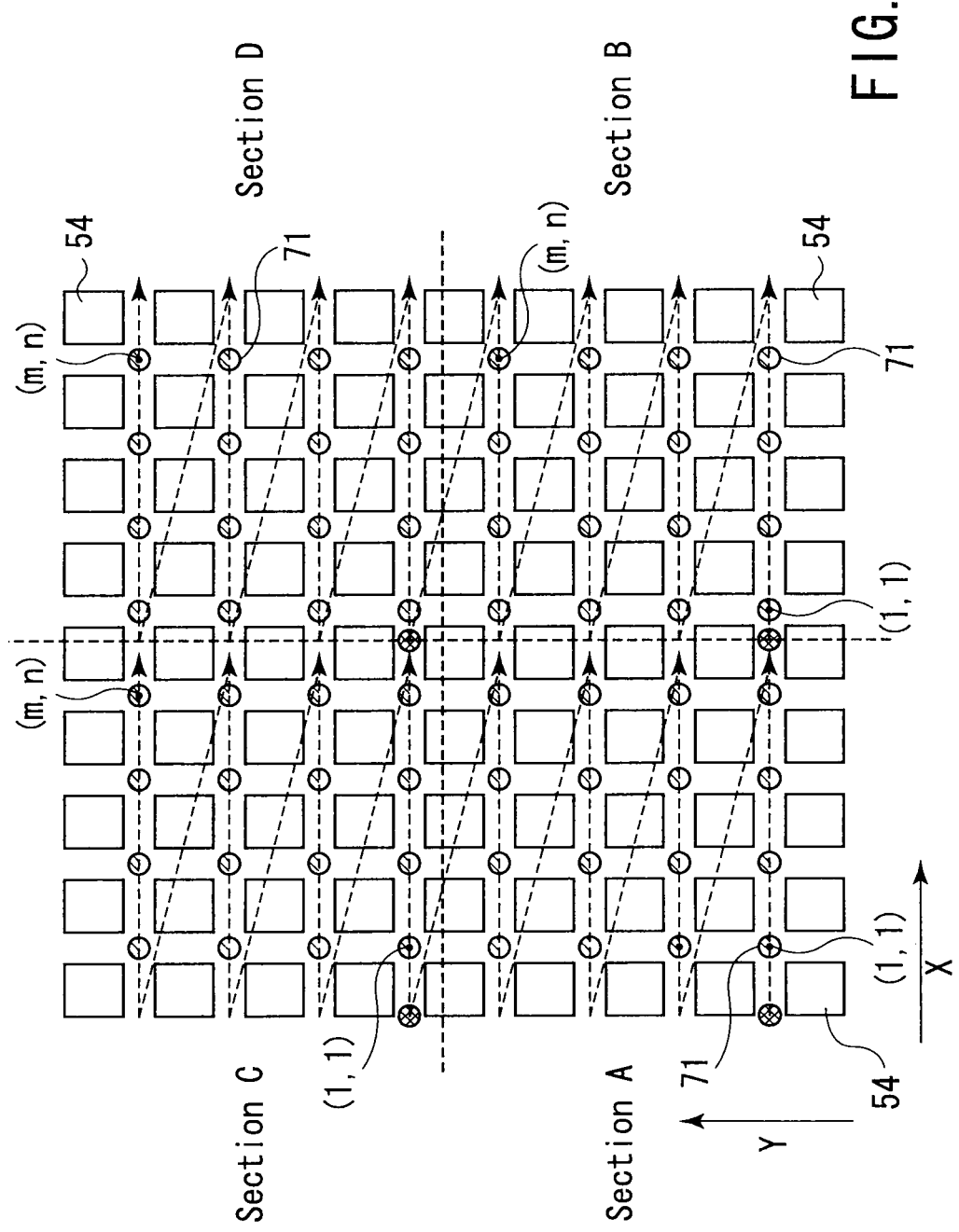
FIG. 10 is a view showing parallel photoacoustic scanning in this embodiment.

FIGS. 8A and 10 show a scanning sequence for shortening the time required for photoacoustic scanning for one volume. The two-dimensional array of the optical fibers 71 and conversion elements 54 is divided into a plurality of sections. Referring to FIGS. 8B and 10, the two-dimensional array of the optical fibers 71 and conversion elements 54 is divided into four sections A, B, C, and D. The number of optical fibers 71 and the number of conversion elements 54 included in the section A are the same as those in each of the sections B, C, and D. Assume that m×n optical fibers 71 are included in each section.

In each section, light irradiation and acoustic wave detection are repeated m×n times in the same operation sequence as that shown in FIG. 8A while the light irradiation position is moved. That is, the optical fibers 71 are selected one by one at predetermined intervals in the array order. As a consequence, the subjected is repeatedly irradiated with light while the light irradiation position is moved. The acoustic waves generated in the subject by each light irradiation operation are detected by the four adjacent conversion elements 54 around each light irradiation position within an interval before the next light irradiation operation. The four detected electrical signals are provided with delay times necessary to form a reception convergence point at a position of the depth L immediately below the light irradiation position, and are added.

In the four sections, the above light irradiation and acoustic wave detection are synchronously repeated. Acoustic wave crosstalk between the sections can be reduced or avoided by keeping predetermined distances between the light irradiation positions of light beams simultaneously applied between the sections. In other words, a section size (n×m) is determined in accordance with the distances required to reduce or avoid acoustic wave crosstalk between the sections.

Figure 11:
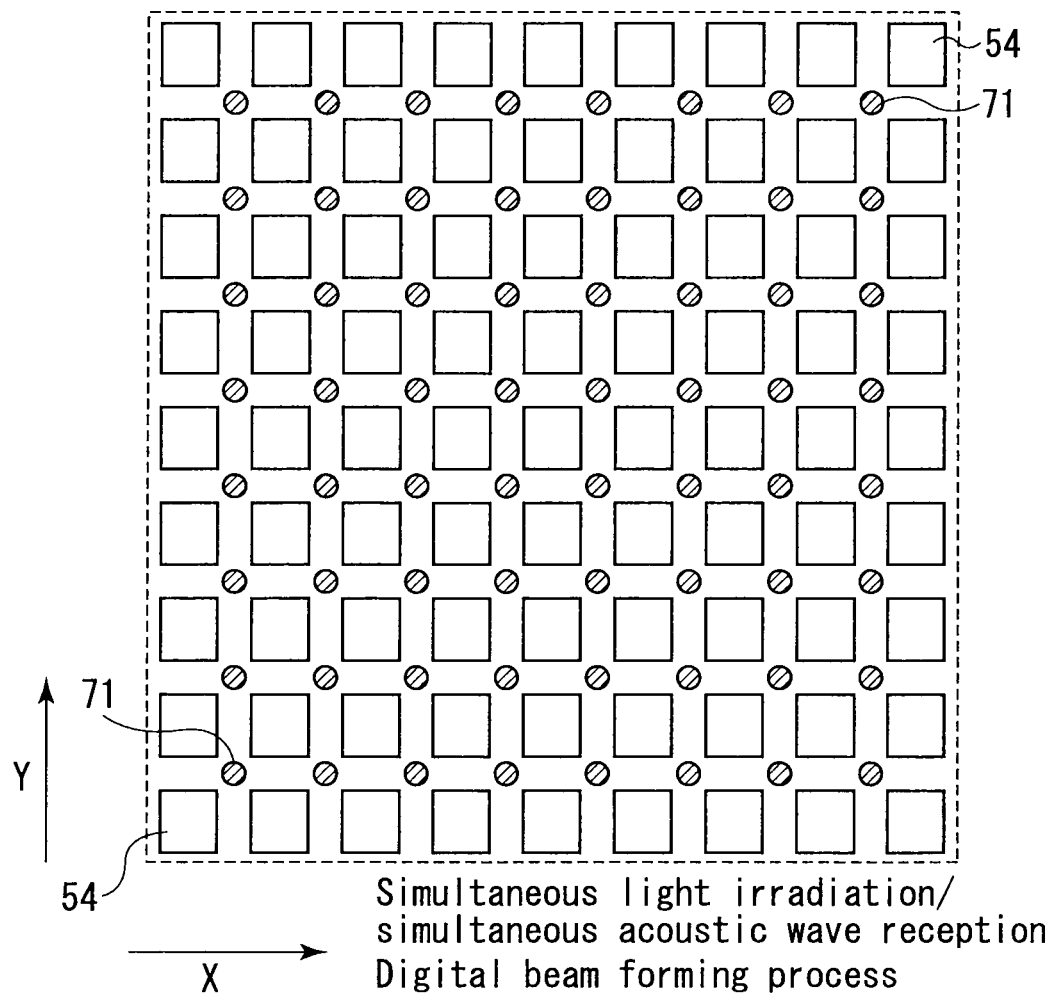
FIG. 11 is a view showing simultaneous photoacoustic scanning in this embodiment.

FIG. 11 shows a method of further shortening the time required for photoacoustic scanning for one volume. Light beams are simultaneously applied from all the optical fibers 71 two-dimensionally arranged in an M×N matrix onto the subject. Immediately after the light irradiation, acoustic waves are detected by all the conversion elements 54 two-dimensionally arranged in an (M+1)×(N+1) matrix. The transmission/reception unit 22 generates M×N reception signals corresponding to the light irradiation positions (1, 1) to (M, N) from the (M+1)×(N+1) detected electrical signals. Each reception signal is generated by adding electrical signals (actually digital data) obtained by the four or more conversion elements 54 around each light irradiation position, with delay times being given to the respective signals.

Figure 12A:
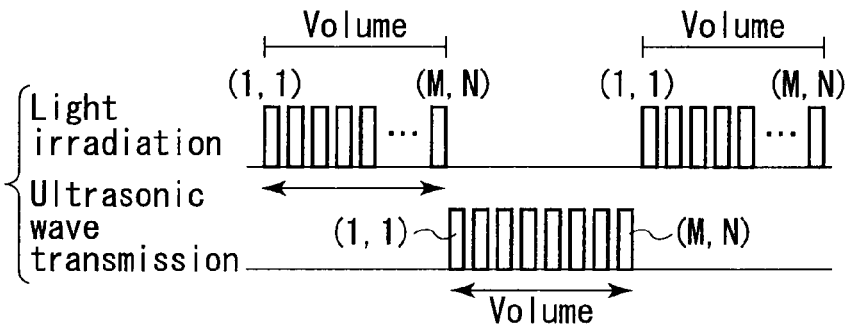
FIGS. 12A to 12D are timing charts showing variations of photoacoustic scanning and ultrasonic scanning in this embodiment.

As shown in FIG. 12A, photoacoustic scanning for one volume and ultrasonic scanning for one volume are alternately performed. A plurality of ultrasonic scanning lines correspond to a plurality of light irradiation positions. A plurality of (M×N in this case) ultrasonic scanning lines pass through the positions (1, 1) to (M, N) and are set in a direction perpendicular to the flat surface of the two-dimensional array of the optical fibers 71 and conversion elements 54. A transmission convergence point and reception convergence point are set at the depth L as in the case with a reception convergence point in photoacoustic scanning. Ultrasonic scanning for one volume is completed by repeating ultrasonic wave transmission and echo reception with respect to the M×N ultrasonic scanning lines constituting one volume.

Alternately performing photoacoustic scanning for one volume and ultrasonic scanning for one volume with respect to the same volume make it possible to acquire living body function volume data and tissue morphology volume data for the same volume which are close to each other in time, i.e., differ from each other only by a scanning time for one volume.

Although the above description has exemplified the case wherein a reception convergence point is set on the normal to the surface of the conversion element array, the position of a convergence point can be arbitrarily set by controlling the delay times between the reception signals obtained from the conversion elements 54.

Figure 12B:
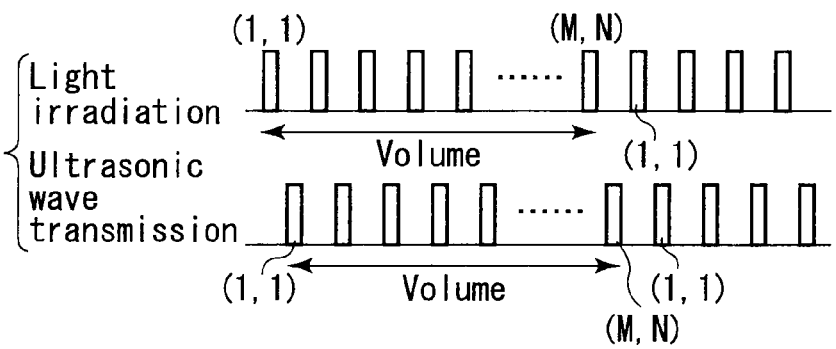

Photoacoustic scanning and ultrasonic scanning can be modified as follows. Referring to FIG. 12A, photoacoustic scanning and ultrasonic scanning are alternately performed on a volume basis. As shown in FIG. 12B, however, photoacoustic scanning and ultrasonic scanning may be alternately performed on a scanning line basis. After light irradiation is performed at the first position in photoacoustic scanning and the resultant acoustic wave is detected, an ultrasonic wave is transmitted to an ultrasonic scanning line corresponding to the first position, and the resultant echo is received. Light irradiation is then performed at the second position next to the first position in photoacoustic scanning, and the resultant acoustic wave is detected. Thereafter, an ultrasonic wave is transmitted to an ultrasonic scanning line corresponding to the second position, and the resultant echo is received. Repeating this operation can greatly reduce the differences in timing between data in a predetermined direction. Even when an organ moving fast or the blood is to be measured, living body function volume data and tissue morphology volume data about the same volume can be measured in almost the same time phase. When the amount of light transmitted is to be increased to improve the reception sensitivity in photoacoustic scanning, the number of times of irradiation per unit time must be decreased to ensure the safety of the subject. To this end, as shown in FIG. 12D, the number of times of scanning per unit time in the photoacoustic scanning method is preferably set to be smaller than that in the ultrasonic scanning method.

Figure 12C:
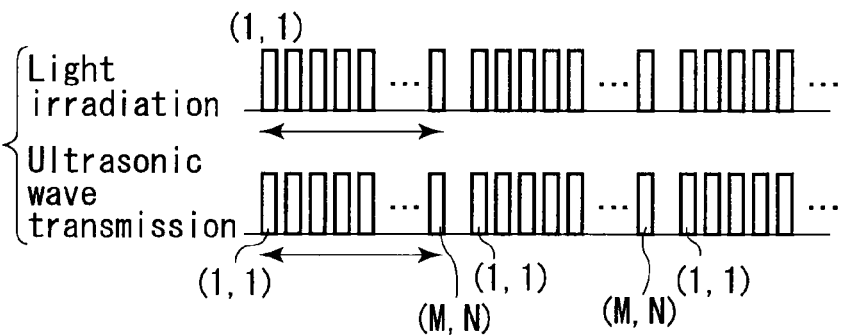
Figure 12D:
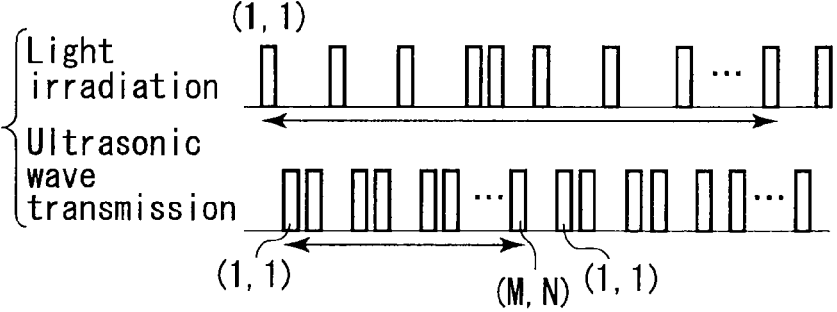

As shown in FIG. 12C, light irradiation and acoustic wave detection in photoacoustic scanning may be performed simultaneously with ultrasonic wave transmission and echo reception in ultrasonic scanning. Since there is no difference in acquisition timing between data, a measurement target moving fast can be measured more accurately than by the above scanning method based on the above scanning unit. In this simultaneous scanning method, if the frequency of an acoustic wave in photoacoustic scanning is equal to that of an ultrasonic wave in ultrasonic scanning, it is impossible to separate an acoustic wave component and echo component from a reception signal. However, an output from the A/D convertor 60 of the signal processing unit 25 can be directly stored in the display image memory 63, and hence the image data memory A 61 and image data memory B 62 can be omitted. Furthermore, there is no need to combine photoacoustic image data and ultrasonic image data. On the other hand, a conversion element 54 which can be vibrated at two separate frequencies can separate an acoustic wave component and echo component. As disclosed in Jpn. Pat. Appln. KOKAI Publication Nos. 61-100237 and 62-39761, this type of conversion element 54 is obtained by joining two piezoelectric elements having different thicknesses and can receive ultrasonic waves having two different frequencies.

If, therefore, for example, the frequency of an acoustic wave in the photoacoustic scanning method and the frequency of an ultrasonic wave in ultrasonic scanning are set to 1.5 MHz and 3 MHz, respectively, even when these signals are simultaneously received by the conversion element 54, photoacoustic image data and ultrasonic image data can be independently generated by discriminating the signals using the filter 66 of the transmission/reception unit 22. In addition, these image data can be identified by colors and displayed on the CRT monitor 65 of the display unit 6.

Figure 13A:
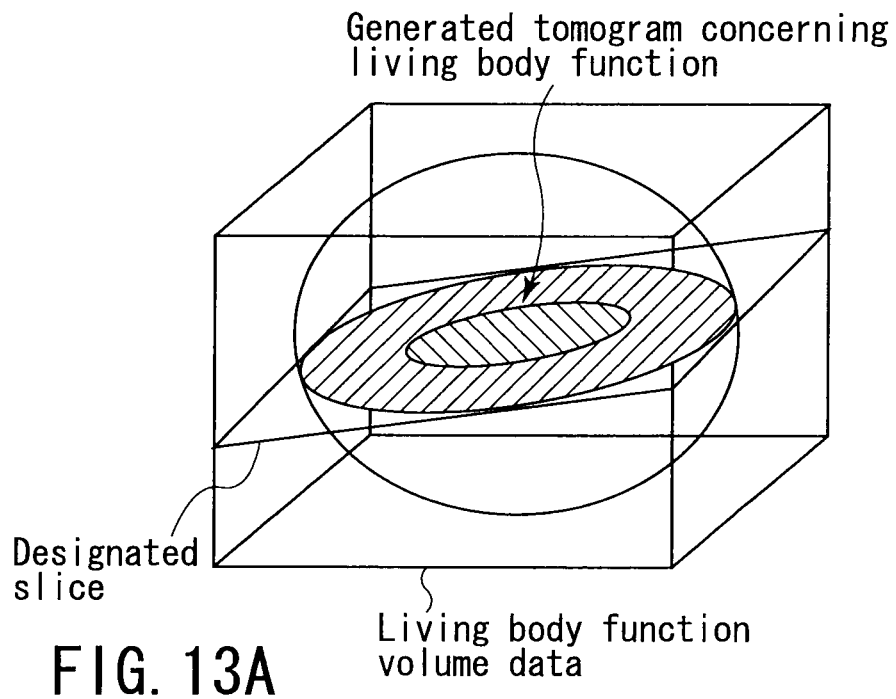
FIGS. 13A and 13B are schematic views showing image data about a living body function and image data about a tissue morphology which are generated by a signal processing unit in FIG. 1.
Figure 13B:
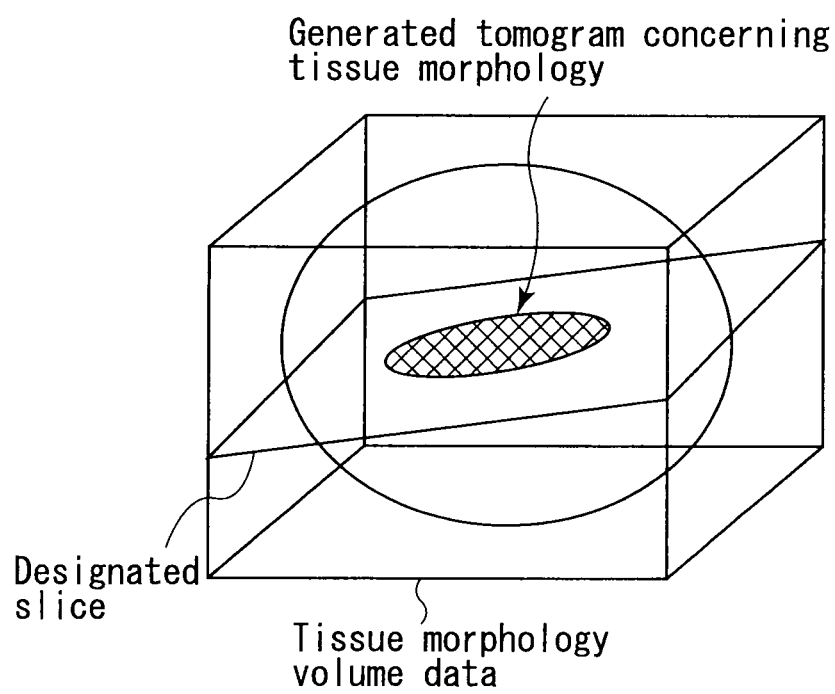

In display operation, as shown in FIGS. 13A and 13B, the data of a slice designated by the operator is read out from the living body function volume data stored in the image data memory A 61, and is spatially interpolated when it is read out, thereby generating tomogram data about the living body function of the designated slice. The data of the same slice is read out from the tissue morphology volume data stored in the image data memory B 62, and is spatially interpolated when it is read out, thereby generating tomogram data about the tissue morphology of the designated slice. The tomogram data about the living body function is arranged in one frame in the display image memory 63, together with the tomogram data about the tissue morphology of the same slice, and is displayed on the CRT monitor 65 through the convertor 64. In addition, the tomogram data about the living body function is converted into a color map. This color map is superimposed on the tomogram data about the tissue morphology in the display image memory 63 to be displayed on the CRT monitor 65.

As described above, since a photoacoustic image and ultrasonic image can be acquired by using the same conversion elements 54, the respective images can be accurately superimposed and displayed. In generating a photoacoustic image, in particular, a so-called phased addition scheme of adding acoustic reception signals obtained from many conversion elements 54 while matching their phases. Even if, therefore, for example, the light applied to the subject 7 is scattered or diffused, the source of acoustic waves can be accurately grasped.

In the above case, ultrasonic image data are acquired after the acquisition of photoacoustic image data. However, there is no limitation to the acquisition order of these image data. Alternatively, a plurality of photoacoustic image data and a plurality of ultrasonic image data may be acquired, and the former and latter may be stored in the image data memory A 61 and the image data memory B 62, respectively. Desired images may then be selected from the image data memory A 61 and image data memory B 62 and combined in the display image memory 63.

To acquire photoacoustic image data, light beams having different wavelengths may be used determine the content of one substance. How the content of, for example, hemoglobin is measured will be described. As mentioned above, hemoglobin in the living body absorbs light in the range of 600 nm to 1,000 nm. Deoxyhemoglobin absorbs more light having a wavelength near 600 nm than oxyhemoglobin does. On the other hand, the amount of light absorbed by oxyhemoglobin absorbs more light having a wavelength near 1,000 nm than deoxyhemoglobin does. Using this difference in absorption property makes it possible to independently quantify oxyhemoglobin and deoxyhemoglobin in the living body or obtain the total amount of both types of hemoglobin. The above 1,000 nm Nd:YAG laser and a 633 nm He—Ne gas laser may be used, and the measurement results obtained by the respective wavelengths may be identified and displayed in different colors. In this case, although a photoacoustic image may be superimposed on an ultrasonic image, they may be displayed side by side.

The content of a substance other than hemoglobin, for example, cholesterol or glucose, may be measured in the same region in the subject 7 by using monochromatic light having an optimal wavelength and by performing the same procedure as described above. The measurement result and the measurement result on hemoglobin may be identified and displayed in different colors. In this case, too, the display method is not specifically limited. Although the photoacoustic image and ultrasonic image may be superimposed and displayed, they may be displayed side by side.

In addition, harmonic imaging may be used as an ultrasonic image generating method. In the photoacoustic scanning method, the frequency spectrum of an acoustic wave ranges from 200 kHz to 2 MHz, with 1 MHz being the center frequency. The conversion elements 54 of the electroacoustic conversion unit 23 must have properties that correspond to such frequency components. This frequency is lower than the center frequency (for example, fo: 3.5 MHz) in general ultrasonic scanning.

Since the same conversion elements 54 are used to acquire both photoacoustic image data and ultrasonic image data, the ultrasonic image obtained by the conventional ultrasonic scanning method inevitably deteriorates in spatial resolution. It will be described how ultrasonic image data should be acquired by the harmonic imaging method in order to solve this problem. The harmonic imaging method effectively utilizes the ultrasonic nonlinear phenomenon that occurs in the tissue of the subject 7. When, for example, an ultrasonic pulse with the center frequency fo is applied to the subject 7, a second harmonic component (2fo) is newly generated due to the nonlinear phenomenon in the tissue to be examined. The conversion element 54 receives this harmonic component, together with a fundamental wave component (fo). The generation of this harmonic component depends on the tissue properties of the subject 7 and also on the propagation distance to a reflecting region or ultrasonic intensity at the reflecting region.

In ultrasonic scanning, some of the transmission ultrasonic waves applied to the subject 7 are reflected by the interface between organs of the subject 7, which differ in acoustic impedance, or by a tissue. From the ultrasonic waves reflected, ultrasonic pulses having a center frequency 2fo are newly generated due to the nonlinear properties of the tissue. Therefore, the reception ultrasonic wave that is reflected by the tissue in the subject 7 and returns to the conversion element 54 contains both an ultrasonic pulse (fundamental wave component) having the center frequency fo at the time of transmission and an ultrasonic pulse (harmonic component) having the center frequency 2fo.

The frequency spectrum of the transmission ultrasonic wave at this time is distributed and centered on the center frequency fo. In contrast, the frequency spectrum of the reception ultrasonic wave is made up of a fundamental wave component distributed and centered on fo and a harmonic component distributed and centered on 2fo. Generally, a harmonic component is smaller than a fundamental wave component by about 20 dB. As is known, the harmonic component is generated since the propagation speed of an ultrasonic pulse in the subject tissue depends on the sound pressure of an ultrasonic wave, and this distorts the waveform of a reception signal.

The conversion element 54 converts a reception ultrasonic wave from the subject 7 from an ultrasonic wave to an electrical signal (ultrasonic reception signal). The ultrasonic reception signal is sent to the filter 66 of the signal processing unit 25 through the transmission/reception unit 22. The filter 66 has a bandpass characteristic centered on 2fo and a bandpass characteristic (not shown) centered on fo. In the harmonic imaging method, the filter 66 extracts a second harmonic component. The output of the filter 66 is stored in the image data memory B 62 via the logarithmic transformation unit 58, envelope detector 59, and A/D convertor 60. In the photoacoustic scanning method, the filter 66 extracts a fundamental wave component, and the output of the filter 66 is stored in the image data memory B 62 via the logarithmic transformation unit 58, envelope detector 59, and A/D convertor 60, as in the first embodiment.

The system control unit 4 reads the ultrasonic image data stored in the image data memory B 62 and the photoacoustic image data stored in the image data memory A 61. The system control unit 4 then combines these data in the display image memory 63, and displays the resultant image on the CRT monitor 65 via the convertor 64.

As described above, ultrasonic image data is generated from a frequency component twice in frequency than a fundamental wave component. Therefore, even if the same conversion elements 54 are used to acquire both photoacoustic image data and ultrasonic image data, a photoacoustic image can be superimposed and displayed on a high-resolution ultrasonic image. In addition, since these two types of image data can be simultaneously acquired and displayed, an apparatus with excellent operability can be provided.

According to the above description, in photoacoustic scanning, the four electrical signals obtained by the four conversion elements 54 around an irradiation position are subjected to phased addition to give directivity to the reception signal. When the subject 7 is irradiated with light from the optical fiber 71, the irradiation light travels straight while maintaining its small diameter. That is, it exhibits strong directivity. Therefore, a photoacoustic image can be generated without performing phased addition processing at the time of reception of acoustic waves. The hemoglobin in the blood in the subject 7 absorbs the energy of irradiation light from the optical fiber 71 and produces acoustic waves. These acoustic waves are converted into electrical signals by the four conversion elements 54 around the light irradiation position. The four electrical signals substantially pass through the reception delay circuits 56 and added by the adder 57 without being given delay times. Since the number of vibrators used for reception can be greatly reduced, the optical fibers 71 provided at end portions can be effectively used. This makes it possible to obtain a wide image width (viewing width).

Figure 14:
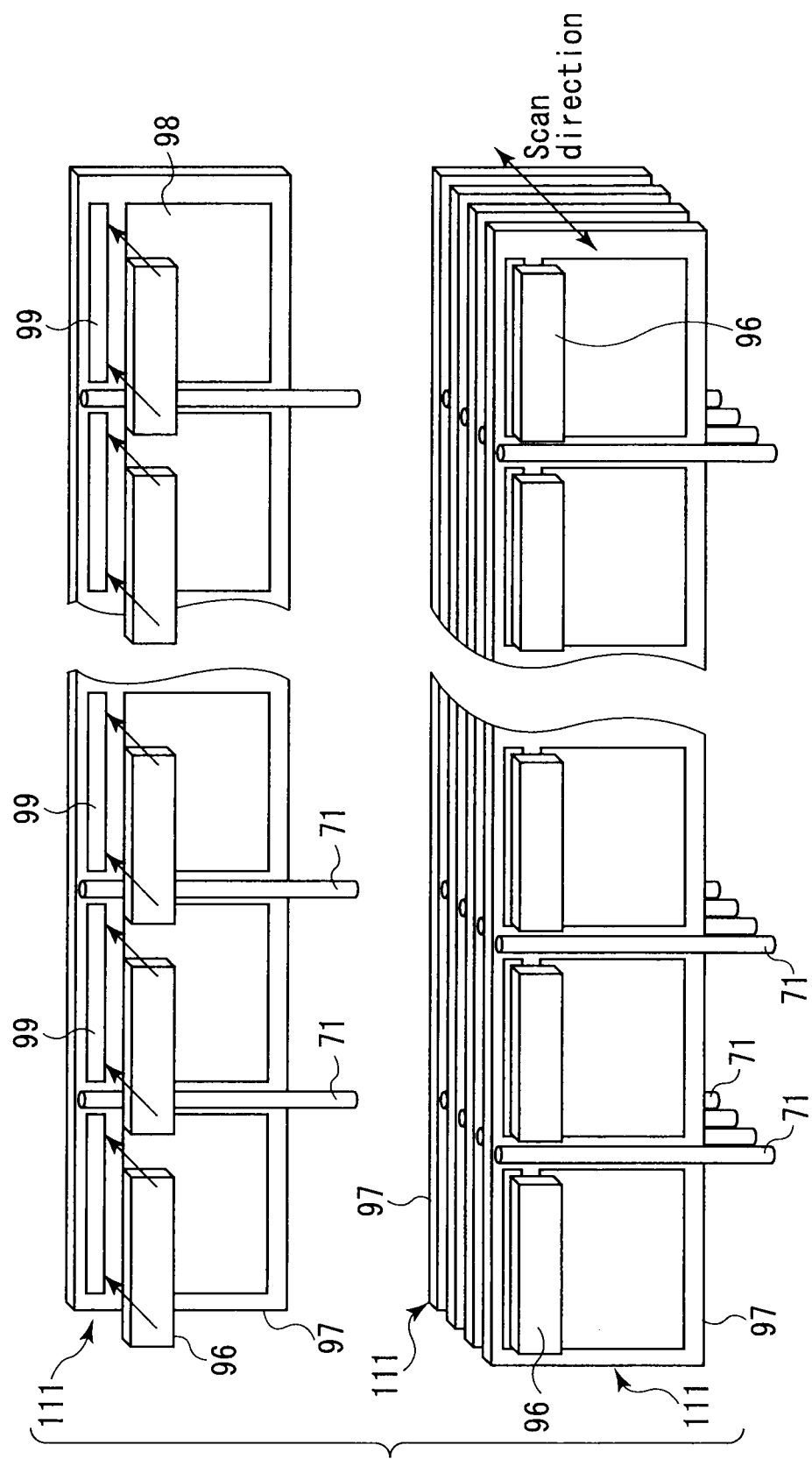
FIG. 14 is a view showing a method of forming the array structure of an irradiation unit and electroacoustic conversion unit in an applicator in FIG. 4.

FIG. 14 shows an example of a method of manufacturing an electroacoustic conversion unit according to this embodiment. For example, a plurality of signal-side electrodes 98 are formed at predetermined intervals on a flexible circuit (FPC) 97 that is 0.05 mm thick. Likewise, a plurality of ground-side electrodes 99 are formed at predetermined intervals on the FPC 97. The signal-side electrode and ground-side electrode of a vibrator 96 having a piezoelectric member made of PZNT or PZT are electrically connected to the signal-side electrode 98 and ground-side electrode 99, respectively, by sputtering Au or the like. An optical fiber 71 having a diameter of, for example, 0.2 mm is bonded between the adjacent vibrators 96. Transducer units 111, each thus configured, are stacked and bonded together with an adhesive.

According to this method, an electroacoustic conversion unit having a light transmission property can be easily manufactured by using optical fibers.

Note that the present invention is not limited to the above embodiment, and can be embodied in practice by modifying constituent elements without departing from the spirit or scope of the invention. In addition, various inventions can be formed by proper combinations of a plurality of disclosed constituent elements. For example, several constituent elements may be omitted from the all the constituent elements in the embodiment. Modifications of this embodiment will be described below.

Figure 15A:
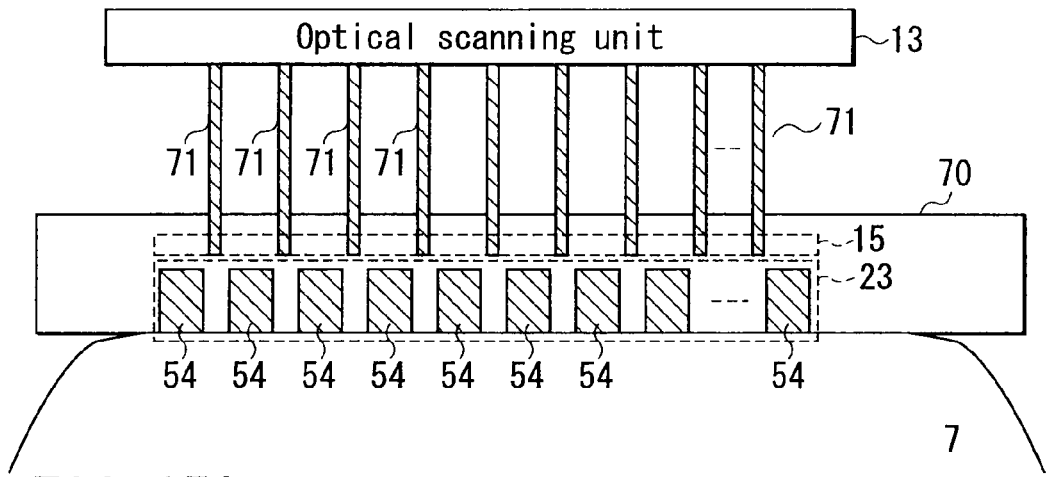
FIGS. 15A and 15B are views showing another structure of the applicator in FIG. 1.

According to the above description, the optical fibers 71 are laid in the gaps between the conversion elements 54. In this case, acoustic coupling occurs between the respective adjacent conversion elements 54, because the optical fibers 71 are inserted in their gaps. Consequently, each conversion element may fail to function as an independent element. Hence, the acoustic coupling may degrade both the photoacoustic image and the ultrasonic image in terms of quality. As shown in FIG. 15A, light emitted from the irradiation unit 15 is applied to the subject 7 through the electroacoustic conversion unit 23. That is, the electroacoustic conversion unit 23 is made of a material which can transmit light. The conversion elements 54 of the electroacoustic conversion unit 23 are formed as follows. A PZNT single-crystal wafer made of transparent piezoelectric material is polished to a predetermined thickness t. The resultant single-crystal plate is cut by a dicing saw into pieces in the form of a two-dimensional array with a pitch d. The gap between any two adjacent pieces, having a width b, is filled with an optically transparent resin 80. The resin 80 is cured. Electrodes 73-1 are formed by sputtering on the first surfaces of the single-crystal elements arrayed two-dimensionally. Electrodes 73-2 are formed by sputtering on the second surfaces of the elements by sputtering. An acoustic matching layer 74 and protective film 75 are stacked, one upon another, on each surface on which the electrode 73-2 is mounted. Note that both the acoustic matching layer 74 and the protective film 75 are made of optically transparent resin. An electrode 73 is made of, for example, transparent, conductive material such as ITO (indium-tin-oxide) or $In_2O_3$ (Sn), used for a liquid crystal display, plasma display, and the like. Thus, a transparent, conductive material is used for the electrodes 73, and an optically transparent resin is used for the acoustic matching layer 74 and protective film 75. A resin 80 fills the gaps between the conversion elements 54. In addition, a transparent piezoelectric single crystal is used for each conversion element 54. The electroacoustic conversion unit 23 formed by fixing these materials on a support 69 made of a transparent resin can provide an optically transparent unit. Therefore, light emitted from the irradiation unit 15 can pass through the electro-acoustic conversion unit 23 and can be applied to the subject 7.

Figure 15B:
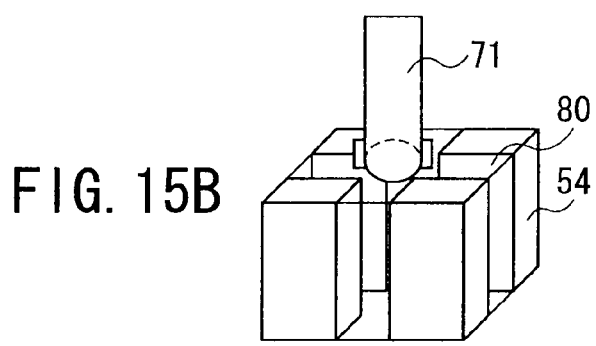

According to the above description, the intervals of the optical fibers 71 are determined by the intervals of the conversion elements 54. In the case shown in FIGS. 15A and 15B, there is no such restriction. The intervals of the optical fibers 71 determine scan intervals in photoacoustic scanning. Photoacoustic images with a high scan density can therefore be obtained. The high-density scanning can improve the image quality, particularly if the spatial resolution of an image is determined by the directivity of irradiation light.

Figure 16:
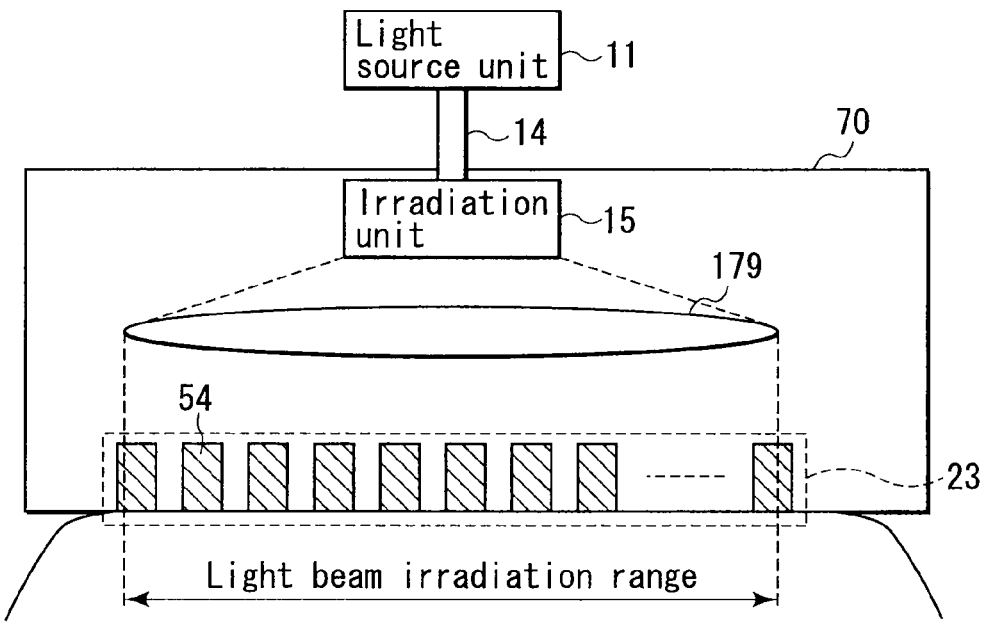
FIG. 16 is a view showing still another structure of the applicator in FIG. 1.

In the case of simultaneous light irradiation shown in FIG. 11, as shown in FIG. 16, the diffused light output from the irradiation unit 15 may be converted into a parallel beam through the waveguide unit 14 constituted by one or a plurality of optical fibers 71. The entire area of the light transmission type electroacoustic conversion unit 23 may be irradiated with these light beams.

Figure 17A:
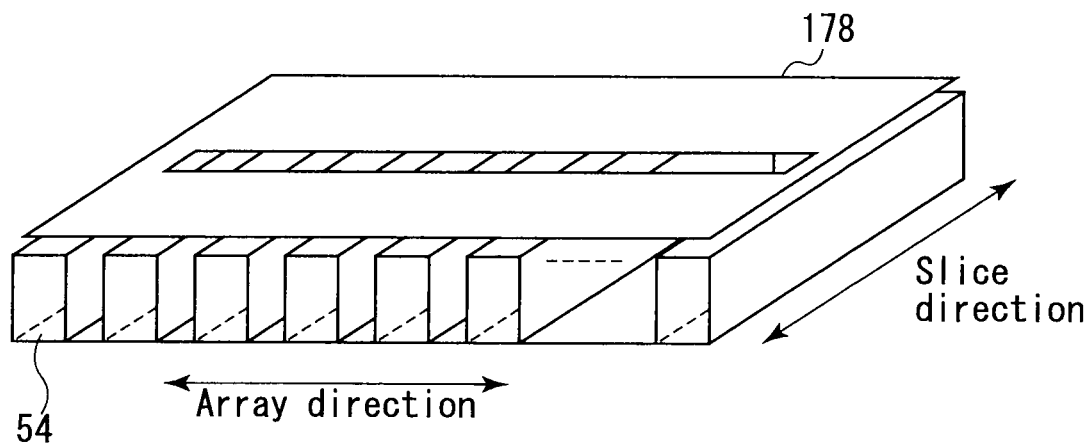
FIGS. 17A and 17B are views showing still another structure of the applicator in FIG. 1.
Figure 17B:
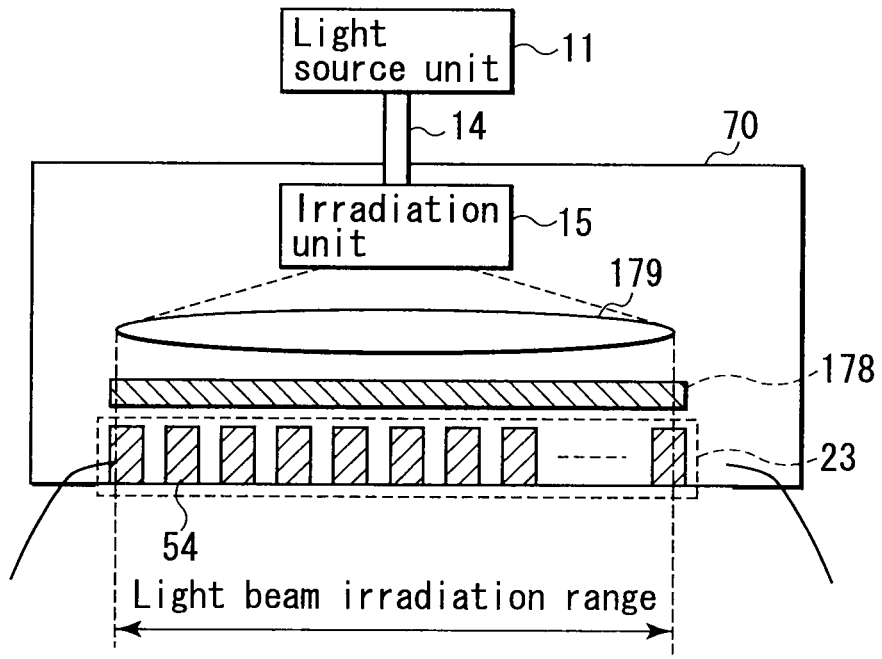

The above optical scanning unit 13 moves the light irradiation position by sequentially selecting the plurality of optical fibers 71 arrayed one by one. According to this method, many optical fibers 71 in the waveguide unit 14 and the optical scanning unit 13 which selects them are required. This will complicate the apparatus. In order to improve the problem in the generation of such irradiation light, as shown in FIGS. 17A and 17B, a slit plate 178 is placed parallel to the array surface of the conversion elements 54. A slit is formed almost in the middle of the plate 178 and extends in the array direction of the conversion elements 54. The beam of light passing through the slit has a large width in the array direction of the conversion elements 54, and a small width in the slice direction perpendicular to this array direction. As shown in FIG. 17B, the applicator 70 has a lens 179 in addition to the slit plate 178. The lens 179 converts the diffused light output from the irradiation unit 15 into a parallel beam. The waveguide unit 14 can directly guide the light supplied to the irradiation unit 15 from the light source unit 11 or optical multiplexing unit 12. Hence, the optical scanning unit 13 is unnecessary. The waveguide unit 14 is not limited to the optical fibers 71, and one channel may be used as long as sufficient power can be obtained.

The monochromatic light generated by the light source unit 11 is guided to the irradiation unit 15 of the applicator 70 by the waveguide unit 14 constituted by, for example, the optical fibers 71. The light is then diffused and radiated from the distal end portion of the irradiation unit 15. This diffused light is converted into a parallel beam by the lens 179 and supplied to the slit of the slit plate 178. The beam width of the light in the array direction and the beam width of the light in the slit direction, which passes through the slit of the slit plate 78 are set by the widths of the slit in the respective directions. The light, now having its width reduced in the slice direction as it passes through the slit, passes through the optically transparent electroacoustic conversion unit 23 and is radiated within the light beam irradiation range of the subject 7 shown in FIG. 17B. The hemoglobin in the blood of the subject 7 absorbs this light and generates acoustic waves. The acoustic waves are converted into electrical signals by one or a plurality of rows of conversion elements 54 corresponding to the slit. As in the above case, a plurality of reception signals corresponding to one row of light irradiation positions corresponding to the slit are generated by phased addition of the electrical signals. While the slit plate 178 reciprocates, light continuously or intermittently radiated, and the conversion elements 54 corresponding to the respective positions on the slit repeatedly detect acoustic waves. When the slit plate 178 moves along the forward or backward path, photoacoustic scanning for one volume is completed.

The use of the slit plate 178 can greatly decrease the number of optical fibers 71 in the waveguide unit 14, and hence can make the optical scanning unit 13 unnecessary. In addition, since irradiation light is continuously radiated in the array direction, the scan density can be arbitrarily set by setting delay times at the time of reception. The restrictions imposed on the use of the optical fibers 71 can be eliminated.

The same effects as those obtained by using the slit plate 178 can also be obtained by forming the irradiation unit 15 from a plurality of optical fibers 72 each having a short axial length, forming the waveguide unit 14 from optical fibers 71 equal in number to one row of optical fibers 72, and providing a mechanism of moving the waveguide unit 14 in the same manner as the slit plate 178. In the arrangement shown in FIGS. 18A and 18B, the optical scanning unit 13 sequentially selects one optical fiber 71 from one row of optical fibers 71 in synchronism with the intermittent movement of the waveguide unit 14, thereby realizing the photoacoustic scanning operation shown in FIG. 7.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. A non-invasive subject-information imaging apparatus comprising:
    a light generating unit which generates light containing a specific wavelength component;
    a plurality of light irradiation units which radiate the light generated by the light generating unit into a subject to be examined;
    a waveguide unit including a plurality of optical fibers, and which guides the light generated by the light generating unit to the irradiation unit;
    a plurality of two-dimensionally arrayed electroacoustic transducer elements;
    a transmitter which transmits ultrasonic waves to the subject by driving the electroacoustic transducer elements, and wherein the plurality of two-dimensionally arrayed electroacoustic transducer elements convert into electrical signals both acoustic waves generated by irradiating light onto the subject and acoustic waves generated by transmitting the ultrasonic waves onto the subject;
    a receiving unit which generates a reception signal having reception directivity from the electrical signals converted by the electroacoustic transducer elements; and
    a filter which discriminates from the reception signal (i) a reception signal corresponding to acoustic waves generated in the subject by light radiated from the light irradiation units and (ii) a reception signal corresponding to echoes generated in the subject upon transmission of the ultrasonic waves;
    a signal processor which generates volume data of a living body function by processing the reception signal corresponding to acoustic waves generated in the subject by light radiated from the light irradiation units, and which generates volume data of a tissue morphology by processing the reception signal corresponding to echoes generated in the subject upon transmission of the ultrasonic waves,
    wherein the light irradiation units are formed by the end portions of the optical fibers, each end portion of the optical fibers is surrounded by four electroacoustic transducer elements, and the light irradiation units and the electroacoustic transducer elements are formed integrally as a single common body interface.

2. The apparatus according to claim 1, wherein the electroacoustic transducer elements are vertically and horizontally arrayed with predetermined gaps therebetween, and the plurality of light irradiation units are discretely arranged in the gaps.

3. The apparatus according to claim 2, wherein the end portions of the optical fibers are arranged in the gaps discretely and in two dimensions.

4. The apparatus according to claim 3, further comprising:
an optical scanner which sequentially irradiates the subject with light from the end portions of the optical fibers.

5. The apparatus according to claim 4, wherein the receiving unit generates a reception signal corresponding to acoustic waves generated by irradiation of the light, from electrical signals from a predetermined number of electroacoustic transducer elements located near an end portion of an optical fiber which has radiated the light.

6. An apparatus according to claim 3, further comprising:
an optical scanner which simultaneously radiates light beams from end portions of not less than two optical fibers whose end portions are spaced apart by not less than a predetermined distance.

7. The apparatus according to claim 6, wherein the receiving unit generates a reception signal corresponding to acoustic waves generated by irradiation of the light from electrical signals provided by a predetermined number of electroacoustic transducer elements located near an end portion of an optical fiber which has radiated the light.

8. The apparatus according to claim 3, wherein light beams are simultaneously radiated from the end potions of the optical fibers.

9. The apparatus according to claim 8, wherein the receiving unit generates a reception signal corresponding to each of the end portions of the optical fibers from electrical signals produced by a predetermined number of electroacoustic transducer elements located near the end portion of the optical fibers.

10. The apparatus according to claim 3, wherein photoacoustic scanning for generating the volume data of the living body function and ultrasonic scanning for generating the volume data about the tissue morphology are alternately performed.

11. The apparatus according to claim 3, wherein the irradiation of light from the end portions of the optical fibers performed to generate the volume data of the living body function and the transmission of the ultrasonic wave by the electroacoustic transducer elements performed to generate the volume data of the tissue morphology, are alternately performed.

12. The apparatus according to claim 2, wherein the electroacoustic elements are received in an optically transparent material and vertically and horizontally arrayed with predetermined gaps therebetween, and
the end portions of the optical fibers are arranged such that light radiated from the end portions reaches the subject after passing through the material.

13. The apparatus according to claim 12, further comprising:
an optical scanner which sequentially irradiates the subject with light from the end portions of the optical fibers.

14. An apparatus according to claim 12, further comprising:
an optical scanner which simultaneously radiates light beams from end portions of not less than two optical fibers whose end portions are spaced apart by not less than a predetermined distance.

15. The apparatus according to claim 12, wherein light beams are simultaneously radiated from the end potions of the optical fibers.

16. The apparatus according to claim 1, wherein the signal processor generates a two-dimensional slice of the volume data of living body function image data and tissue morphology image data.

17. The apparatus according to claim 16, wherein the living body function image data and the tissue morphology image data are displayed side by side on a single screen, or one of the living body function image data and the tissue morphology image data is displayed.

18. The apparatus according to claim 16, wherein the living body function image data and the tissue morphology image data are superimposed and displayed.

19. The apparatus according to claim 1, wherein the light is radiated from a plurality of light irradiation positions in turn.

20. The apparatus according to claim 1, wherein the light is radiated from a plurality of light irradiation positions simultaneously.

21. The apparatus according to claim 1, wherein the light is simultaneously radiated from a predetermined number of discrete light irradiation positions.

22. The apparatus according to claim 1, wherein the irradiation of light and the transmission of an ultrasonic wave are alternately performed.

23. The apparatus according to claim 1, wherein the signal processor comprises:
a first image data generator which receives an electrical signal output from the electroacoustic transducer elements and generates first image data regarding a volume on the basis of acoustic waves caused by irradiation of light;
a second image data generator which receives an electrical signal output from the electroacoustic transducer elements and generates second image data regarding the volume on the basis of acoustic waves caused by the transmission of the ultrasonic waves; and
a display unit which displays the first image data and the second image data.

24. The apparatus according to claim 1, wherein the transmitter uses all or a subset of the electroacoustic transducer elements, said subset of the electroacoustic transducer elements being adjacent to the transmitter.

25. The apparatus according to claim 1, wherein the wavelength of the light falls within a spectral range between about 530 nm and 1,300 nm.

26. A non-invasive subject-information imaging method comprising:
generating light containing a specific wavelength component using a light generating unit;
radiating the generated light into a subject to be examined using a plurality of light irradiation units, the light irradiation units formed by end portions of a plurality of optical fibers;
transmitting ultrasonic waves to the subject by driving a plurality of two-dimensionally arranged electroacoustic transducer elements, each end portion of the optical fibers is surrounded by four electroacoustic transducer elements, and the light irradiation unit and the electroacoustic transducer elements formed integrally as a single common body interface;
causing the plurality of two-dimensionally arrayed electroacoustic transducer elements to convert acoustic waves from the subject into electrical signals, the plurality of two-dimensionally arrayed electroacoustic transducer elements converting into electrical signals both acoustic waves generated by irradiating light onto the subject and acoustic waves generated by transmitting the ultrasonic waves onto the subject;
generating a reception signal having reception directivity from the electrical signals converted by the electroacoustic transducer elements;
discriminating from the reception signal (i) a reception signal corresponding to acoustic waves generated in the subject by light radiated from the light irradiation units and (ii) a reception signal corresponding to echoes generated in the subject upon transmission of the ultrasonic waves; and generating volume data of a living body function by processing the reception signal corresponding to acoustic waves generated in the subject by the radiated light, and generating volume data of a tissue morphology by processing the reception signal corresponding to echoes generated in the subject upon transmission of the ultrasonic waves.

* * * * *